(12) United States Patent
MacDonald et al.

(10) Patent No.: US 6,979,308 B1
(45) Date of Patent: Dec. 27, 2005

(54) BIOREACTOR DESIGN AND PROCESS FOR ENGINEERING TISSUE FROM CELLS

(75) Inventors: Jeffrey M. MacDonald, Chapel Hill, NC (US); Stephen P. Wolfe, Chapel Hill, NC (US)

(73) Assignee: University of North Carolina at Chapel Hill, Chapel Hill, NC (US)

( * ) Notice: Subject to any disclaimer, the term of this patent is extended or adjusted under 35 U.S.C. 154(b) by 307 days.

(21) Appl. No.: 09/586,981

(22) Filed: Jun. 5, 2000

Related U.S. Application Data

(60) Provisional application No. 60/137,594, filed on Jun. 3, 1999.

(51) Int. Cl.$^7$ .................. A61M 37/00; A61M 31/00; C02F 1/44; C12N 5/08; C12M 1/12
(52) U.S. Cl. ............... 604/6.09; 604/522; 210/321.89; 210/321.64; 210/314; 435/297.1
(58) Field of Search ...................... 604/4.01, 5.01, 604/6.09, 6.01, 6.04, 6.14, 7, 23, 500, 522, 604/48; 435/407, 297.1–4, 398, 400, 366, 435/370, 373, 374, 283.1, 289.1, 294.1, 401; 422/44, 45, 48; 210/321.87–89, 321.6, 500.1, 210/500.21, 321.64, 294, 295, 314, 316, 210/321.84, 500.23, 600, 634, 641, 644, 210/645, 255, 194, 195.1, 195.2, 198.1, 200, 210/207, 203, 252, 257.1–2

(56) References Cited

U.S. PATENT DOCUMENTS

| | | | |
|---|---|---|---|
| 4,227,295 | A | 10/1980 | Bodnar et al. |
| 4,440,853 | A | 4/1984 | Michaels et al. |
| 4,442,206 | A | 4/1984 | Michaels et al. |
| 4,833,083 | A | 5/1989 | Saxena |

(Continued)

FOREIGN PATENT DOCUMENTS

EP   0 113 328 A   7/1984

(Continued)

OTHER PUBLICATIONS

Busuttil, R.W. et al., "*The first 100 liver transplants at UCLA*"; Ann. Surg., vol. 206, No. 4, 1987: 387-402.

(Continued)

*Primary Examiner*—Patricia Bianco
*Assistant Examiner*—Leslie Deak
(74) *Attorney, Agent, or Firm*—Gilberto M. Villacorta

(57) ABSTRACT

A scaled-up multi-coaxial fiber bioreactor, and variations of this bioreactor. The device is characterized by a hollow housing and an array of from about 20 to about 400 modules of hollow fibers, where each module includes at least three coaxial semipermeable hollow fibers. The innermost fiber provides a boundary for an innermost compartment which is connected to inlet and outlet ports. Arranged coaxially around the central hollow fiber are several other hollow fibers with their respective compartments, each compartment defined by a respective annular space between adjacent fibers and each including inlet and outlet ports. An outermost compartment for permitting integral aeration is the space between the outer side of the outermost fibers and the inner side of the housing, and has inlet and outlet ports. The hollow housing has inlet and outlet manifolds and flow distributors for each of the compartments. In a preferred embodiment the bioreactor is used as an extracorporeal liver. Liver cells, are introduced into one or more annular compartments and media and aeration are provided in others. Plasma from an ailing patient is introduced into another compartment for biotransformation of blood-borne toxins and biosynthesis of proteins, lipids, and other metabolic products.

37 Claims, 25 Drawing Sheets

U.S. PATENT DOCUMENTS

| | | | |
|---|---|---|---|
| 5,015,585 A | 5/1991 | Robinson | |
| 5,057,428 A * | 10/1991 | Mizutani et al. | 435/293.2 |
| 5,183,566 A | 2/1993 | Darnell et al. | |
| 5,605,835 A | 2/1997 | Hu et al. | |
| 5,622,857 A | 4/1997 | Goffe | |
| 5,827,729 A | 10/1998 | Naughton et al. | |
| 6,218,182 B1 | 4/2001 | Naughton et al. | |
| 6,582,955 B2 * | 6/2003 | Martinez et al. | 435/297.4 |

FOREIGN PATENT DOCUMENTS

| | | |
|---|---|---|
| EP | 0 909 811 A | 4/1999 |

OTHER PUBLICATIONS

Abe, T. et al. "*Efficient membrane and adsorbent for artificial liver support system*"; Therapeutic Apheresis, vol. 4, No. 1, 2000, 26-28.

Xu, A.S.L. et al., *Lineage Biology and Liver.; Principles of Tissue Engineering*, 2$^{nd}$ Ed., Lanza, R.P., Langer, R., & Vacanti, J. (Ed.'s), Academic Press, San Diego, 2000: 559-97.

Brill, S. et al., "*Maturation-dependent changes in the regulation of liver-specific gene expression in embryonal versus adult primary liver cultures*"; Differentiation, vol. 59, 1995: 95-102.

Sigal, S.H. et al., "*Evidence for a terminal differentiation process in the rat liver*"; Differentiation, vol. 59, 1995: 35-42.

Kasai et al., "*Is the biological artificial liver clinically applicable? a historic review of biological artificial liver support systems*"; Artif. Organs, vol. 18, No. 5, 1994: 348-354.

Macdonald, J.M. et al., "*NMR spectroscopy and MRI investigation of a potential bioartificial liver*"; NMR Biomed., vol. 11, 1998: 55-66.

Glacken, M.W. et al., "*Large-scale production of mammalian cells and their products: engineering principles and barriers to scale-up*"; Ann. NY Acad. Sci., vol. 413, 1983: 355-72.

Catapano, G. et al., "*The effect of oxygen transport resistances on the viaility and functions of isolated rat hepatocytes*"; Int. J. Art. Organs, vol. 19, No. 1, 1996: 61-71..

Macdonald, J.M. et al., Bioartificial Livers; *Cell Encapsulation Technology and Therapeutics*, Kuhtreiber, W., Lanza, R.P., Chick, W.L. (Ed.'s), Birkhauser Boston, Cambridge, 1998: 252-86.

Smith, M.D. et al., "*Techniques for measurement of oxygen consumption rates of hepatocytes during attachment and post-attachment*"; Int. J. Artif. Organs, vol. 19, No. 1, 1996: 36-44.

Rotem, A. et al., "*Oxygen uptake rates in cultured rat hepatocytes*"; Biotech. & Bioeng., vol. 40, 1992, 1286-92.

Callies, R. et al., "*Measurements of the growth and distribution of mammalian cells in a hollow-fiber bioreactor using nuclear magnetic resonable imaging*", Bio/Technology, vol. 12, Jan. 1994: 75-78.

Cremer, T. et al., "*Aging in vitro and D-glucose uptake kinetics of diploid human fibroblasts*"; J. Cell. Physiol., vol. 106, 1981:99-108.

Imamura, T. et al., "*Fructose as a carbohydrate source yields stable pH and redox parameters in microcarrier cell culture*"; Anal. Biochem., vol. 124, 1982: 353-58.

Glacken, M., Dissertation, 1987.

Mufti, N.A. et al., "*Induction of cytochrome P-450la1 activity in response to sublethal stresses in microcarrier-attached Hep G2 cells*"; Biotechnol. Prog., vol. 11, 1995: 659-63.

Sato, Y. et al., "*Acute portal hypertension reflecting shear strees as a trigtger of liver regeneration following partial hepatectomy*"; Surg. Today, vol. 27, 1997: 518-26.

Enat, R. et al., "*Hepatocyte proliferation in vitro: its dependence on the use of serum-free hormonally defined medium and substrate of extracellular matrix*"; Proc. Natl. Acad. Sci. U.S.A., vol. 81, Mar. 1984: 1411-15.

Bissell, D.M., "*The role of extracellular matrix in normal liver*"; Scan. J. Gasterenterol. vol. 23, supplement 151, 1988: 1-7.

Brill, S. et al., "*Hepatic progenitor populations in embryonic, neonatal, and adult liver*"; Proc. Soc. Exp. Biol. Med., vol. 204, No. 3, 1993: 261-69.

Rana, et al., 1994.

Block, G.D. et al., "*Population expansion, clonal growth, and specific differentiation patterns in primary cultures of hepatocytes induced by HGF/SF, EGF and TGF-alpha in a chemically defined (HGM) Medium*"; J. Cell Biol., vol. 132, No. 6, Mar. 1996: 1133-49.

Sanchez, A. et al., "*Transforming growth factor-beta (TGF-beta) and EGF promote cord-like structures that indicate terminal differentiation of fetal hepatocytes in primary culture*"; Exp. Cell Res., vol. 242, 1998: 27-37.

Hornicek, F.L. et al.,"*Establishment of primary cell cultures from human and canine parathyroid gland explants*"; Bone & Miner, vol. 4, 1988: 157-65.

Mickelson, J.K. et al., Hepatology, vol. 22, 1995: 866.

Glacken, M., Dissertation, 1987.

Mickelson, J.K. et al., *Hepatology*, vol. 22, 1995: 866.

Rana, et al., *Mol. Cell Biology*, 1994.

* cited by examiner

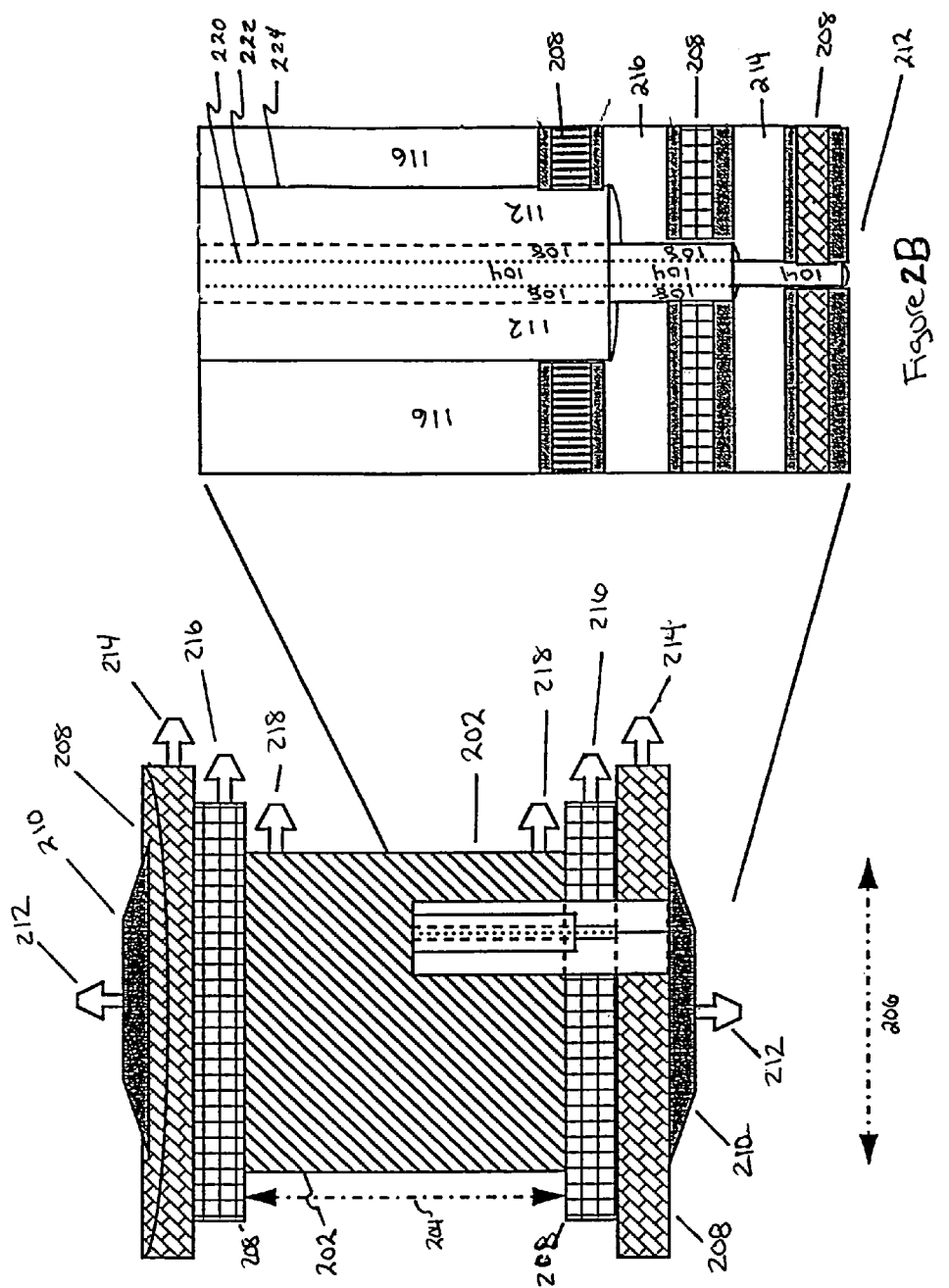

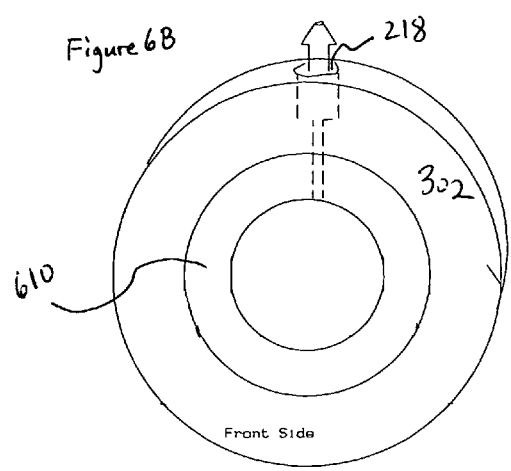
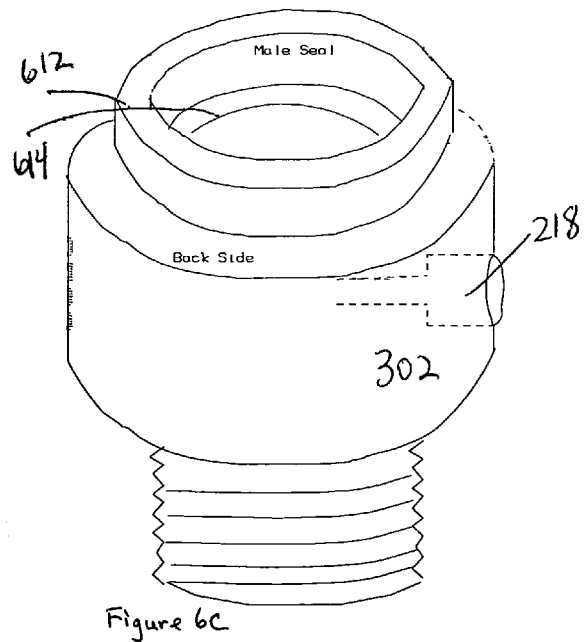
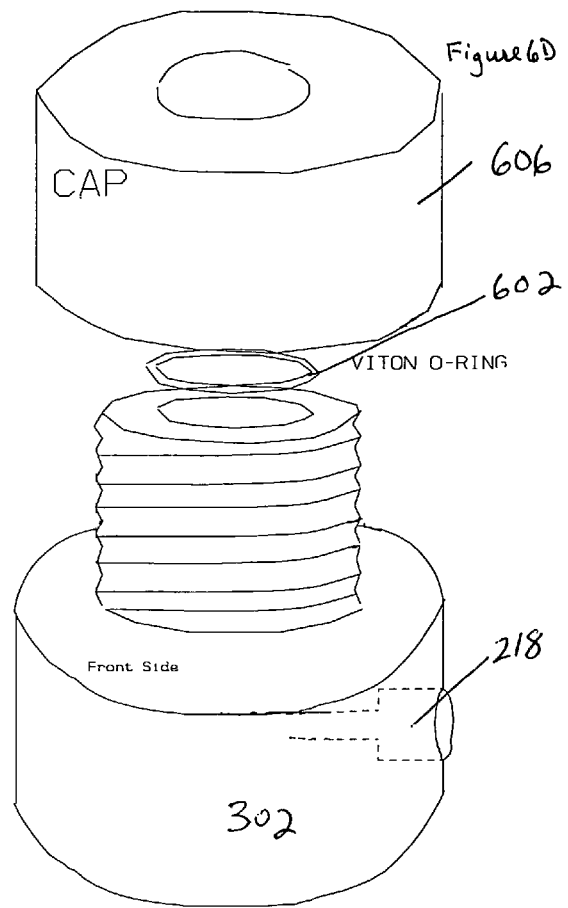

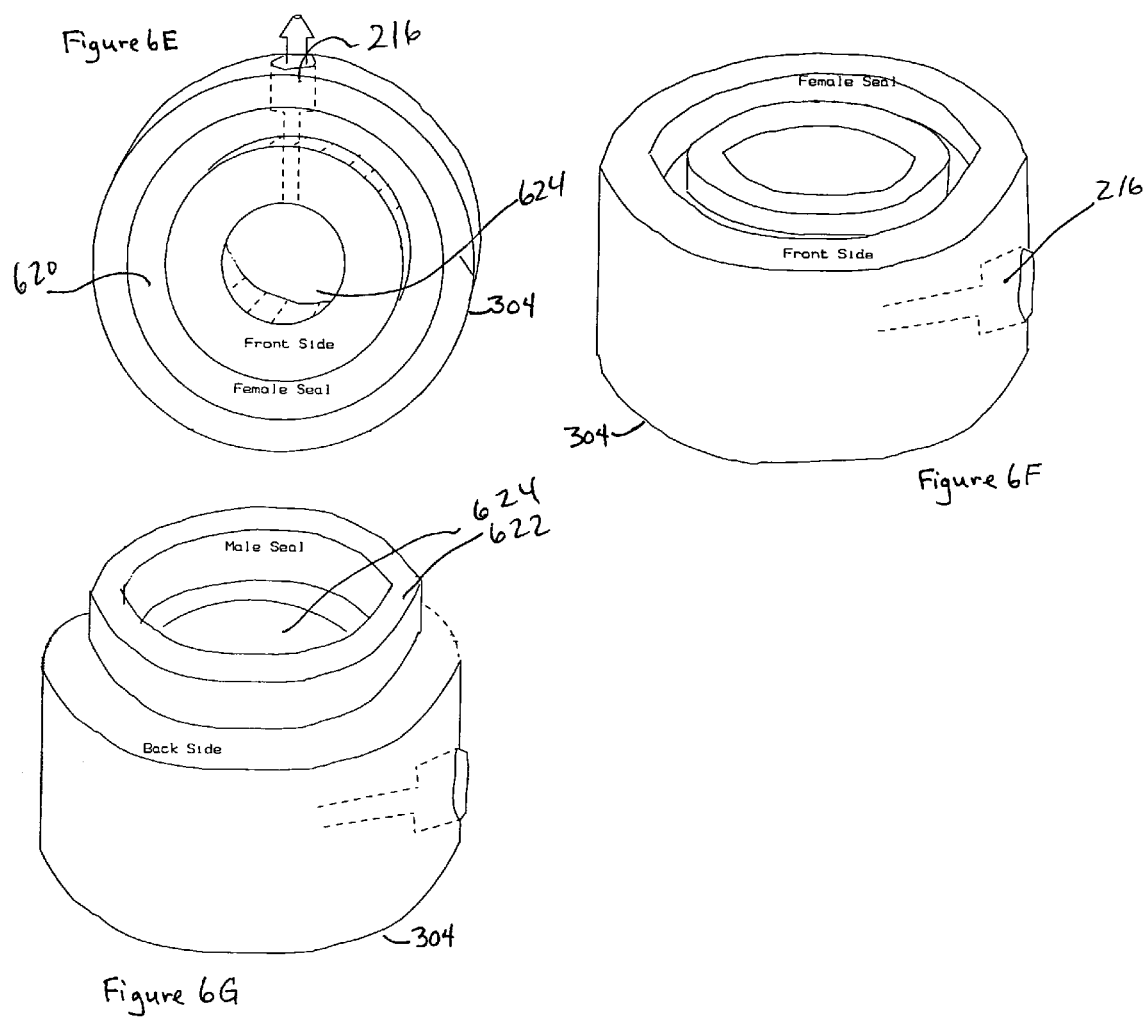

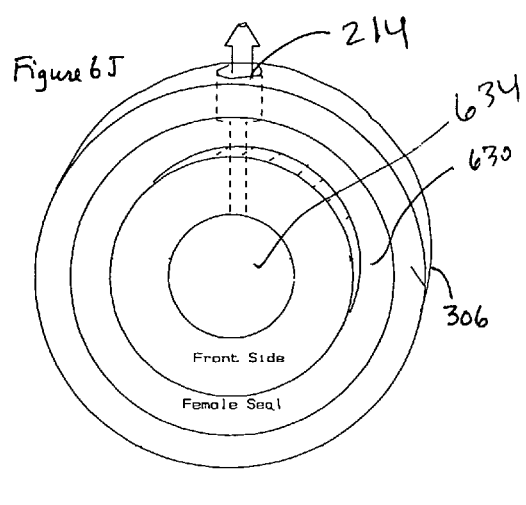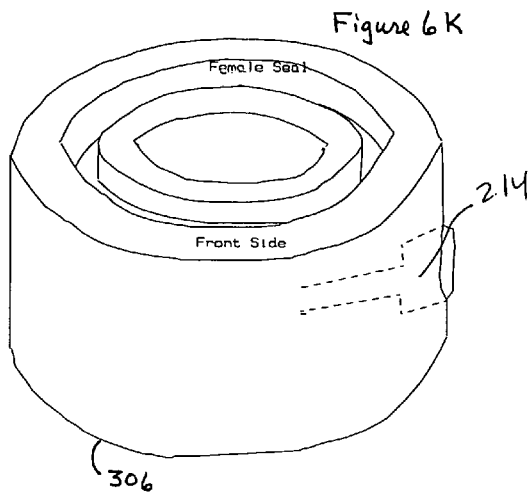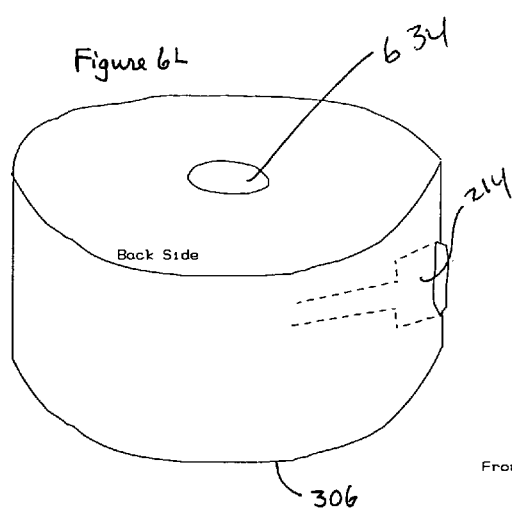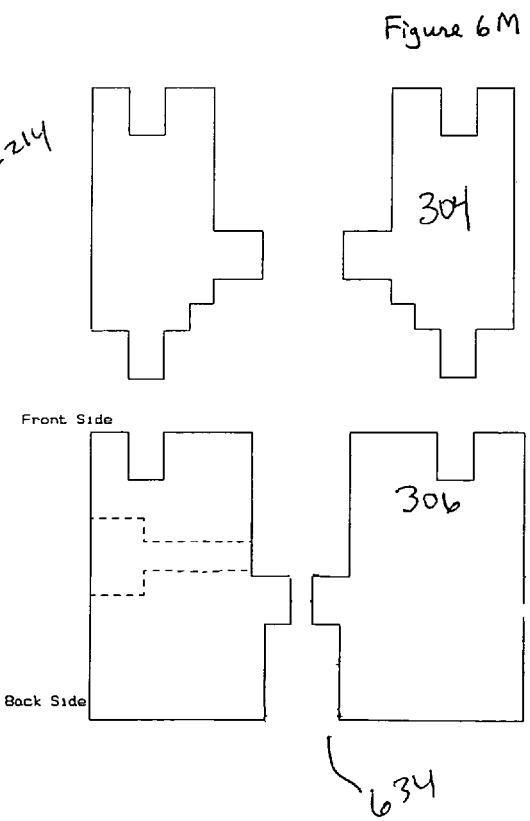

BIOREACTOR DESIGN AND PROCESS FOR ENGINEERING TISSUE FROM CELLS

This application claims priority to U.S. Provisional Application No. 60/137,594, filed Jun. 3, 1999, the complete disclosure of which is incorporated by reference herein.

GOVERNMENT INTERESTS

This invention was made with support under 1 F32 DK09713-01 awarded by the National Institute of Diabetes, Digestive, and Kidney Diseases. The government has certain rights in the invention.

1. FIELD OF THE INVENTION

The present invention relates generally to devices and processes of making and using devices for cell culture. In particular, the present invention relates to devices and processes of making and using devices for growth or maintenance of eukaryotic cells. One embodiment of the invention performs functions of the human liver.

2. BACKGROUND OF THE INVENTION AND RECOGNITION OF THE PROBLEMS

Liver failure is classified into several major types, including acute liver failure, chronic liver disease, and multiorgan failure. The main etiologies of liver failure are viral hepatitis and hepatotoxicity induced by drugs and toxins. Advanced liver failure results in encephalopathy and coma, and may be fatal. Treatment focuses on stabilization of the patient until spontaneous recovery of liver function, or until liver transplantation. In the aggregate, the annual mortality attributable to liver failure exceeds 27,000 annually in the United States.

Artificial organs, which are devices made entirely of non-biological materials, have greatly advanced health care. Artificial organs and tissue substitutes, including kidney dialysis machines, mechanical respirators, cardiac pacemakers, and mechanical heart pumps have sustained many people with desperate life-threatening diseases. The utility of such artificial organs is reflected in their widespread use. Pacemakers, for example, serve admirably as substitutes for their biological analogs.

The artificial kidney, sometimes termed the kidney dialysis machine, illustrates both the benefits and shortcomings of purely artificial organs. Kidney dialysis machines are effective in removing urea, creatinine, water, and excess salts from the blood, thus partly fulfilling major roles of the natural kidney. Clearly, artificial kidneys have postponed deaths of patients in renal failure. However, kidney dialysis machines are insufficiently selective and inappropriately remove biological components, such as steroid hormones, that a functioning natural kidney does not. Consequently, dialysis over an extended period may result in bone loss, clotting irregularities, immunodeficiencies, and sterility.

The patient in hepatic failure, unlike the patient in renal failure, cannot be specifically treated. Renal dialysis, which revolutionized the treatment of renal failure, does not presently have a hepatic equivalent. Currently, the only available treatment for refractory liver failure is hepatic transplantation. Many patients in hepatic failure do not qualify for transplantation because of concomitant infection, or other organ failure. Because of organ shortages and long waiting lists, even those who qualify for liver transplantation often die while awaiting an allograft. UCLA reported that one quarter of their transplant candidates died before a liver could be obtained. Organs suitable for transplant in the pediatric age group are even more scarce (Busuttil, R. W. et al. *Ann Surg* 1987, 206, 387).

The natural liver has four major classes of biochemical functions. First, the liver biosynthesizes a wide range of proteins, including major acellular components of blood, such as serum albumin, alpha-anti-trypsin, alpha-macroglobulin, enzymes, clotting factors, carrier molecules for trace elements, and the apo-lipoproteins. The liver then releases these components to the blood circulation. The liver also maintains appropriate plasma concentrations of amino and fatty acids. Second, the liver has a major role in detoxification reactions. The liver oxidizes or conjugates many harmful external poisons, processes that usually, but not always, diminish the poisonous character of the toxins. The liver also destroys excess hemoglobin, metabolizes the porphyrin molecules of hemoglobin, and recycles the iron component. Third, waste products, such as bilirubin, are conjugated and excreted via the biliary tree. Fourth, the liver synthesizes and secretes the bile salts, which serve as detergents that promote the emulsification and digestion of lipids. The multiplicity and biochemical character of liver function vastly increase the complexity of extracorporeal hepatic support.

Bioartificial organs are artificial organs designed to contain and sustain a viable biological component. Many biological functions are even more complex than simply generating a voltage potential at regular intervals, as occurs in the simplest of pacemakers. Examples include biosynthesis of blood components and catabolic processing of deleterious agents. The liver, endocrine glands, bone marrow, and kidney are prominent in such specialized biochemical functions. Artificial organs without a biological component cannot reproduce the complex biochemical functions executed by these organs.

Historically, non-biologic artificial liver substitutes have depended on hemodialysis and hemoperfusion, but have been of very short-term and highly limited benefit (Abe, T. et al., Therapeutic Apheresis 2000, 4:26). In contrast to purely artificial organs, an effective liver replacement must have a biological component. The liver is the most massive organ in the human body, exclusive of distributed organs such as skin, gut, hematopoietic system, and vasculature. Sustaining a large mass of functioning liver cells in vitro presents a variety of hurdles. At least eight major problems to developing a functional bioartificial liver can be described: 1) growing or obtaining appropriate and viable cells; 2) providing for a critical minimum mass of cells; 3) supplying oxygen to the cells; 4) supplying nutrients to the cells, and removing cell waste products efficiently; 5) limiting shear forces and hydrostatic pressures, 6) inducing or sustaining a differentiated cell phenotype with the capacity for biosynthesis and biotransformation of toxins; 7) maintaining sterility; and 8) preventing liver tissue rejection or lysis by complement.

1) Growing or obtaining appropriate and viable cells. Liver cells for potential use in bioartificial livers can be established cell lines, primary isolates from human or animal livers, or primordial liver cells however, secretion of tumorigenic factors is negatively affecting FDA approval of BAL designs incorporating cell lines (Xu, A. S. L. et al., 2000 in *Lineage Biology and Liver*, Lanza, R. P., Langer R., and Vacanti, J. (Ed.), Academic Press, San Diego, pp. 559–597). Cell lines of liver are available, for example HepG2 and C3A, that express many functions of differentiated liver. Cell lines offer the potential of growing sufficient numbers of cells in an extracorporeal mass cell culture system, or bioreactor, for sustaining a patient because the growth of cell lines is not limited by cell senescence, but by nutrient availability. Primary human or animal liver cells can also be obtained in the numbers required for a functional bioartificial liver. However, the use of human liver for cell preparation is limited by its lack of availability, and the use of animal liver for cell preparation suffers from some degree of cellular incompatibility. Acute cellular incompatibility results from the binding of antibodies that recognize foreign cells followed by the binding of proteins of the complement system and lysis of the foreign cells. Longer-term cellular incompatibility mechanisms also exist, but should not present any problems for the use of bioreactors as interim or "bridge" medical products. A possible alternative to initial inoculation with a large mass of differentiated cells is the expansion of liver stem cells that are progenitors of mature liver cells. Recent reports suggest that liver progenitor cells go through multiple cell divisions on the path toward maturation and differentiation (Brill, S. et al., *Differentiation* 1995, 59, 95; Sigal S. H. et al., *Differentiation* 1995, 59, 35). Suitable control of the growth and differentiation processes with staged application of appropriate cytokines can permit preparation of a clinically useful quantity of cells.

2) Providing for a critical minimum mass of cells. The adult human liver has a mass of about 1400–1600 grams, and features a considerable reserve, or redundant, capacity. It is estimated that human survival can be sustained with about 15–20% of the total liver mass. The figure of 20% of the liver mass corresponds to about $5 \times 10^{10}$ cells (Kasai et al. *Artif Organs* 1994, 18, 348). Most, if not all, previous bioartificial liver designs suffer from a woefully inadequate cell capacity. That is, such devices are capable of sustaining far fewer than $5 \times 10^{10}$ cells, often orders of magnitude fewer cells. Without the cell mass critical for biosynthesis of plasma components and detoxification reactions, these other designs have little clinical utility.

3) Supplying oxygen to the cells. The functional units of most organs such as nephron, acinus, alveoli, microvilli, skin, etc. consists of a capillary bed across which is a physico-chemical gradient. These gradients are controlled by mass transfer effects. Oxygen is the primary nutrient that is limiting in cell cultures (Macdonald, J. M. et al. *NMR Biomed* 1998, 11, 1; Glacken M. W. et al. *Ann NY Acad Sci* 1983, 413, 355). 'Integral' oxygenation, or aeration inside the bioreactor containing the biological or chemical material of interest, greatly enhances mass transfer of oxygen and carbonic acid. The formation of the latter can be used to control pH.

Oxygen is generally the limiting nutrient in hollow fiber bioartificial livers (Catapano, G. et al. *Int J Art Organs* 1996, 19, 61) primarily because hepatocytes are highly aerobic cells which causes problems of oxygen mass transfer. Oxygen has a relatively high diffusion coefficient and its mass transfer from blood in the liver sinusoids to hepatocytes is dominated by diffusion rather than convection (i.e., convection and perfusion are caused by pressure gradients). These effects are because an oxygen molecule is much smaller than other nutrients such as a glucose molecule, or than biosynthetic products such as proteins, and because the hepatocytes generate steep concentration gradients in bioartifical livers. With known rates of oxygen diffusion and oxygen consumption, and reasonable estimates of cell density, the diffusion distance at which oxygen utilization becomes the rate-limiting factor for growth is approximately 200 $\mu$m (Macdonald, J. M. et al., 1999, in *Cell Encapsulation Technology and Therapeutics*, Kuhtreiber, W., Lanza, R. P. and Chick, W. L. (Eds.) Birkhauser Boston, Cambridge, pp. 252–286. In bioartificial livers with serial oxygenation aerated with air, oxygen becomes axially limiting in perfusion media by 25 mm (Macdonald et al., 1999, supra).

Hepatocytes have a high metabolic rate and require a continuous oxygen supply. The oxygen consumption rate ranges from 0.59 to 0.7 $nmole/s/10^6$ cells for HepG2 cells (Smith, M. D. et al *Int J Artif Organs* 1996, 19, 36) and is 0.42 $nmole/s/10^6$ cells for isolated hepatocytes (Rotem, A. et al. *Biotech Bioeng* 1992, 40, 1286). Integral oxygenation, that is, continuous supply of oxygen along the path of media supply to the cells, is essential to supplying oxygen to liver cells. Serial oxygenation, which is oxygenation at one or a few places in the fluid line of media supply cannot sustain the mass of liver cells needed for an effective bioartificial liver. A difficulty with serial oxygenation is that the solubility of oxygen in aqueous media unsupplemented with oxygen carriers is so low that any oxygen present is quickly depleted by cell metabolism. In fact, in longitudinal flow along a conventional bioreactor semipermeable membrane, hepatocytes deplete oxygen within 2.5 centimeters along the path and therefore convective oxygen mass transfer via increasing Starling flow is improved. Increasing flow rates through conventional bioreactors can cause fiber breeches and adversely affect hepatocyte function (Callies, R. et al., Bio/Technology 1994 12:75). Thus, bioartificial liver designs that do not provide for adequate oxygen delivery are able to support only a limited number of cells. In addition, the flux of oxygen in a diffusion-limited system constrains cells to grow very near (less than about 0.2 mm) to the supply of oxygen. For example, U.S. Pat. No. 5,622,857 to Goffe discloses a bioreactor with some coaxial and some parallel semi-permeable hollow fibers. The Goffe design allows integral oxygenation but does not constrain the thickness of the cell compartment. The fiber-to-fiber spacing in that design is 3–5 mm so that there is not strict control of the oxygen diffusion distance. Similarly, U.S. Pat. No. 5,183,566 to Darnell et al. discloses a bioreactor with bundles of hollow fibers in parallel. The Darnell et al. design does not permit a multitude of individual multi-coaxial fiber bundles to be built-up with accurate and reproducible diffusion distances, and the design is not easily scaled-up. The Darnell et al. design uses bundles of parallel fibers, again not effectively addressing the issue of oxygen diffusion. Thus, a need remains for a bioreactor which deals effectively with the diffusion-limited thickness of the cell mass, with providing a critical mass of cells, and with supplying oxygen throughout the length of the bioreactor without adverse shear force effects.

4) Supplying nutrients to the cells, and removing cell waste products efficiently. The issue of supplying nutrients such as carbohydrates, lipids, minerals, and vitamins has been successfully solved by several variants of hollow fiber technology, and these features must be successfully incorporated into any viable bioartificial liver or bioartificial organ design. Similarly, the issue of removing metabolic wastes is usually handled by the same system that supplies the nutrients. The consumption rates for glutamate, pyruvate, and glucose are typically in the range of 0.03 to 0.3 $nmol/s/10^6$ cells, with reasonable assumptions for cell density and growth rate (Cremmer, T. et al. *J Cell Physiol* 1981, 106, 99; Imamura, T. et al. *Anal Biochem* 1982, 124, 353; Glacken, M. Dissertation 1987). The diffusion rates of oxygen in tissue are similar to those of pyruvate in water, and higher than those of glucose. As these consumption rates are less than the oxygen consumption rate, oxygen is the limiting nutrient in most conditions.

5) Limiting shear forces and hydrostatic pressure. For a given bioreactor there is an optimum balance of convection and diffusion for adequate oxygen mass transfer without creation of severe oxygen gradients. For example, using a nontoxic oxygen range, <0.4 mM (solubility constant is 1.06 mM/atm, for air solubility is 0.2 mM at 37° C.), the convective component of oxygen mass transfer should be increased as cells are increasingly farther than 0.2 mm from supply of oxygen (Macdonald et al., 1999, supra.). Although the partial oxygen tension in the liver sinusoid is about 70 mm Hg near the portal triad dropping to 20 mm Hg near the central vein, which equates to a range of 0.096 to 0.027 mM of free oxygen, the hemoglobin-bound oxygen ranges from 6.26 to 2.91 mM. The velocity of blood flow in the liver sinusoid is about 0.02 cm/s while the oxygen diffusion coefficient is about 4 orders-of-magnitude less, or $2 \times 10^{-6}$ $cm^2/s$. However, hepatic function is adversely affected with increasing shear forces, and in vivo hepatocytes are protected by a layer of endothelia and extracellular matrix in the space of Disse. Sufficient shear forces will kill hepatocytes. Others have found that shear forces induce specific cytochrome P450's (Mufti N. A. and Shuler, M. L., *Biotechnol. Prog.*, 1995, 11, 659). A recent study has shown that liver regenerates faster with 90% than with 70% hepatectomy and this was attributed to greater shear forces (Sato, Y. et al., *Surg. Today,* 1997, 27, 518). However, this faster regeneration could also be due to enhanced oxygen, nutrient, and agonist mass transfer. Therefore, there is some maximum level of shear force that hepatocytes can sustain while still displaying optimal function. This maximum level can be increased if a layer of endothelia protects hepatocytes.

To increase convection, hydrostatic pressure gradients are increased. Elevated hydrostatic pressures can implode hepatocytes. Therefore, it is important to stay below these pressures. It is possible to cause 100% mortality of isolated rat hepatocytes by generating hydrostatic pressures of greater than 7 psi (>300 mm Hg) for longer than 2 minutes while inoculating these cells into coaxial bioreactor using a syringe.

6) Inducing or sustaining a differentiated cell phenotype with the capacity for biosynthesis and biotransformation of toxins. The use of the differentiated phenotype of liver cells is necessary to produce a useful bioartificial liver because the specialized functions of the liver, including biosynthesis of blood components and detoxification of toxins, are associated with the differentiated phenotype. These specialized functions are lost in whole, or in part, as the cells dedifferentiate, which often happens in isolated primary cell culture. In contrast, the form of liver cells capable of rapid growth is the dedifferentiated phenotype, leaving the practitioner to balance two opposing needs (Enat, R. et al. *Proc Natl Acad Sci USA,* 1984, 81, 1411). Some reports suggest that the phenotype of liver cells may be modulated by the presence of cytokines and extracellular matrix components. In particular, the extracellular matrix components rich in collagen IV and laminin, produced by the Engelbrech-Holm Sarcoma (EHS) cells and available commercially as MATRIGEL™, when used with hormonally defined media induces a differentiated phenotype (Enat, R. et al., supra; Bissell, D. M. *Scan J Gasterenterol-Suppl* 1988, 151,1; Brill, S. et al. *Proc Soc Exp Biol Med* 1993, 204, 261).

7) Maintaining sterility. The implementation of facile sterilization procedures for bioreactors and associated components is essential for clinical utility of extracorporeal bioartificial organs. Fortunately, the procedures for sterilization are well established, including standard methods both for sterilization of extracorporeal devices and for maintaining asepsis by standard in-line filters.

8) Preventing liver tissue rejection or lysis by complement. Rejection of foreign tissue may occur by a rapid process known as complement-mediated lysis that involves binding of circulating antibodies to the foreign cell surface, attachment of the proteins of the complement system, and lysis of the offending cell. The cell-mediated immune system is responsible for delayed rejection reactions. However, the cell-mediated immune system should not play a major role in bioreactor systems that do not permit direct contact of host and donor cells. Foreign body reactions, for example, against the structural components of bioreactors, are also cell-mediated and should therefore not constitute substantial obstacles.

Needed Improvements.

In view of the above, a clear need exists for bioartificial livers to sustain patients in liver failure. Specifically, a need exists for an improved version of a bioartificial liver that would have a high biological cell capacity in very thin layers of cells, readily accessible to oxygen and nutrients. There is a need for an apparatus or bioreactor, that provides efficient oxygen delivery to large masses of cells in cell culture and permits transfer of beneficial biosynthetic cell products to the patient. Similarly, there exists a need for effective methods of use of such an apparatus.

The problems with existing bioreactor designs include inadequate oxygenation, minimal capacity for the biological cell component, limited capability for removal of toxins, excessive shear and hydrostatic forces, and difficulty in transferring biosynthetic cell products for patient use. In addition, existing bioreactor designs have not dealt effectively with the diffusion-limited thickness of the cell mass, with providing a critical mass of cells, and with supplying oxygen throughout the length of the bioreactor.

3. SUMMARY OF THE INVENTION

It is therefore an object of the present invention to provide varying embodiments of an apparatus which provides efficient oxygen delivery to large masses of cells in a bioreactor cell culture and transfer of beneficial biosynthetic cell products to the patient, and methods of use therefor.

It is a further object of the present invention to provide an apparatus which permits cells to be contained in a thin annular space adjacent to continuously oxygenated and flowing nutrient medium that provides essential oxygen and nutrients and carries away metabolic products.

It is a still further object of the present invention to provide an apparatus for the collection of the biosynthetic products of large masses of cells in a bioreactor.

It is a still further object of the present invention to provide an apparatus to detoxify blood or plasma from a patient unable to remove or inactivate these toxins.

It is a still further object of the present invention to provide an apparatus to serve as a substitute liver.

The present invention provides a scaled-up multi-coaxial hollow fiber bioreactor, having: a housing having an inner side; and an array of about 20 to about 400 modules of hollow fibers, each module having at least three coaxial semipermeable hollow fibers. The module of hollow fibers has a first fiber nested within a second fiber; the second fiber nested within a third fiber; and so on. Each fiber has an inner side and an outer side. A first compartment is defined by the inner side of the first fiber, and has at least one first inlet port and at least one first outlet port. A second compartment is defined by a first annular space between the outer side of the first fiber and the inner side of the second fiber, and has at least one second inlet port and at least one second outlet port. A third compartment is defined by a second annular space between the outer side of the second fiber and the inner side of the third fiber, and has at least one third inlet port and at least one third outlet port; and successive compartments are defined by the adjacent fibers. An outermost compartment for permitting integral aeration is defined by an annular space between the outer side of the outermost fiber and the inner side of the housing, and has at least one outermost inlet port, and at least one outermost outlet port. The housing has at least one inlet manifold and at least one outlet manifold for each compartment.

An additional embodiment of the present invention features a serially-linked bioreactor with multiple scaled-up multi-coaxial hollow fiber bioreactors in which two or more compartments are connected in a continuous and serial manner. This implementation is particularly useful for both the biotransformation of toxins in patient plasma and the biosynthesis of plasma components to supplement patient blood.

A further embodiment of the present invention includes a one-sided multi-coaxial hollow fiber bioreactor that is particularly adapted to NMR studies and uses in which access to all ports from one side or one end is necessary.

Yet a further embodiment of the present invention includes a two-sided multi-coaxial hollow fiber bioreactor that is particularly adapted to small scale investigations.

A still further embodiment of the present invention includes a tight-packed hollow fiber bioreactor. This implementation is particularly useful for high density culture of cells in a compact arrangement and is suitable for both the transformation of toxins in patient plasma and the biosynthesis of plasma components to supplement patient blood.

The bioreactor of the present invention, when used as a bioartificial liver, has a modular design to allow an easy adjustment in liver functional capacity depending on the weight of the patient, whether that patient is infant, child, adolescent or adult, man or woman, and on the degree of remaining liver function in the patient. The bioreactor of the present invention further has both plasma and nutrient medium compartments to permit the biotransformation of toxins in the patient plasma and to enhance the effective transfer of biosynthetic products from the bioartificial liver to the patient. When used with liver or other cells, this invention is useful in the preparation of biosynthetic products for patients, in experimental use, and use as a supplemental biotransformation apparatus for detoxification of blood. The toxins in the blood may include, but are in no way limited to, metabolic wastes, products of cell or erythrocyte break-down, overdoses of ethical pharmacologic agents such as acetaminophen, and overdoses of illicit pharmacologic agents. Ease of manufacture of the invention enables cost-effective commercial development.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

4. BRIEF DESCRIPTION OF THE DRAWINGS

FIG. 2A illustrates an elevation view of a multi-coaxial fiber bioreactor.

FIG. 2B illustrates an enlarged view of a detail of a multi-coaxial fiber unit.

Figure 3A:
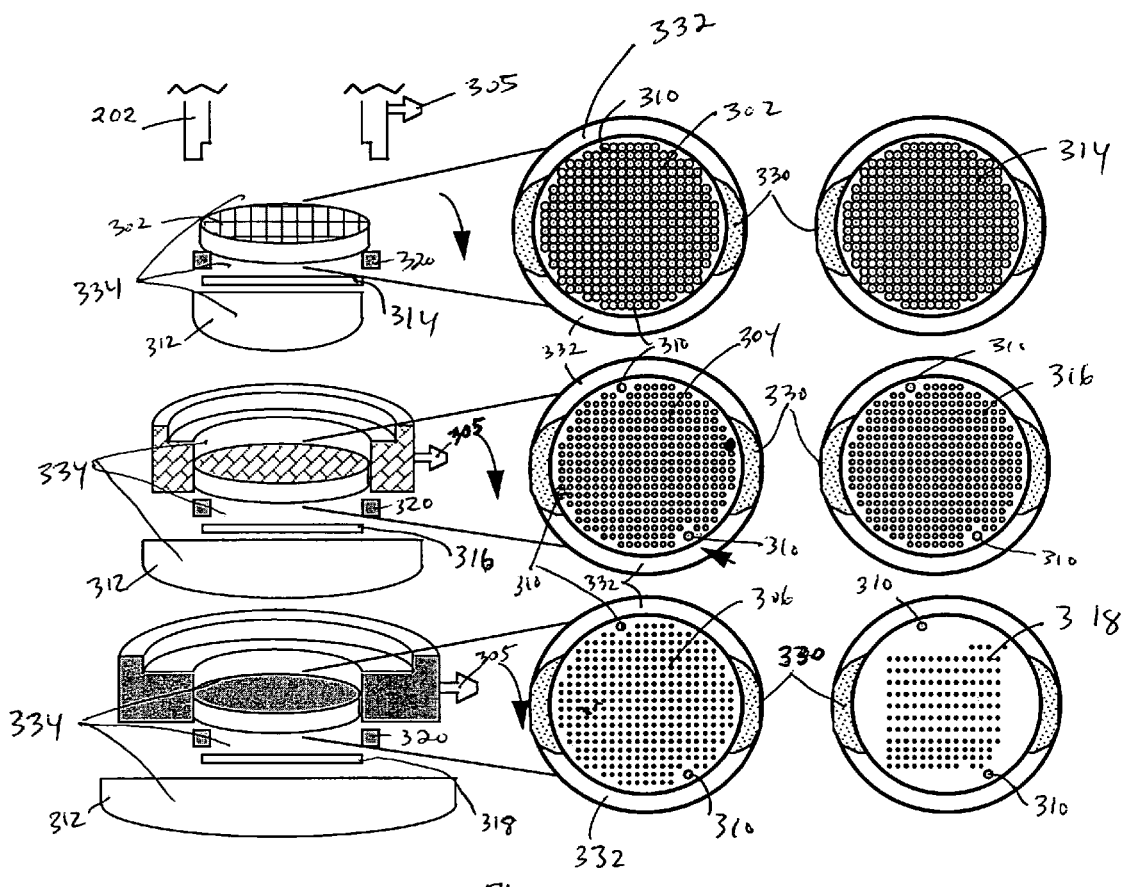
FIG. 3A illustrates a set of components for centering the fibers.
Figure 3B:
FIG. 3B illustrates a detail of the spacer.
Figure 3C:
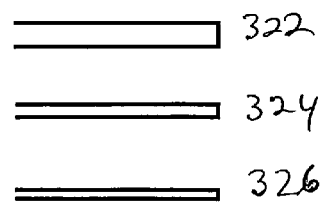
FIG. 3C illustrates the fiber clips.
Figure 3D:
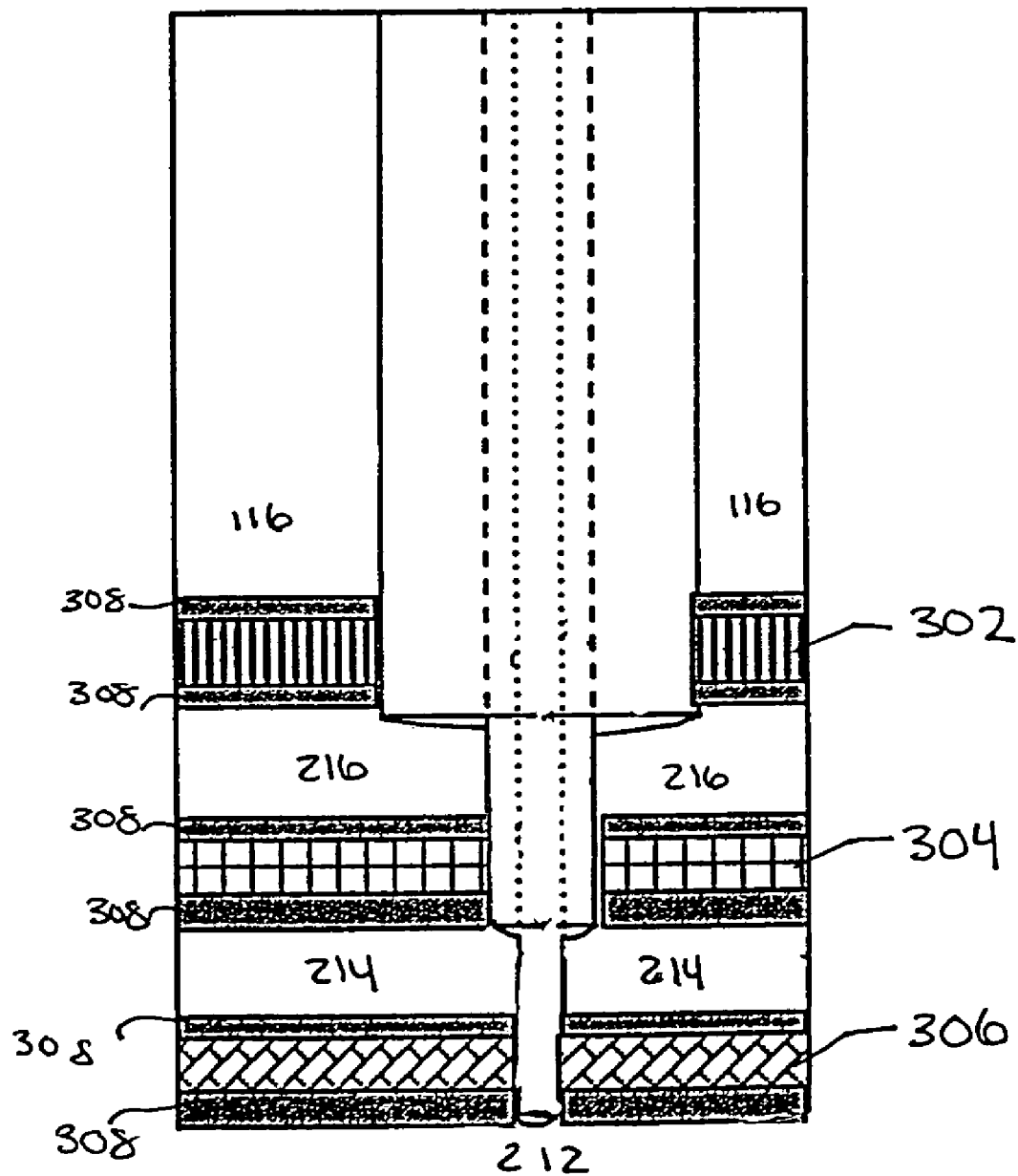
FIG. 3D illustrates a detail of the arrangement of manifolds for the bioreactor.
Figure 3E:
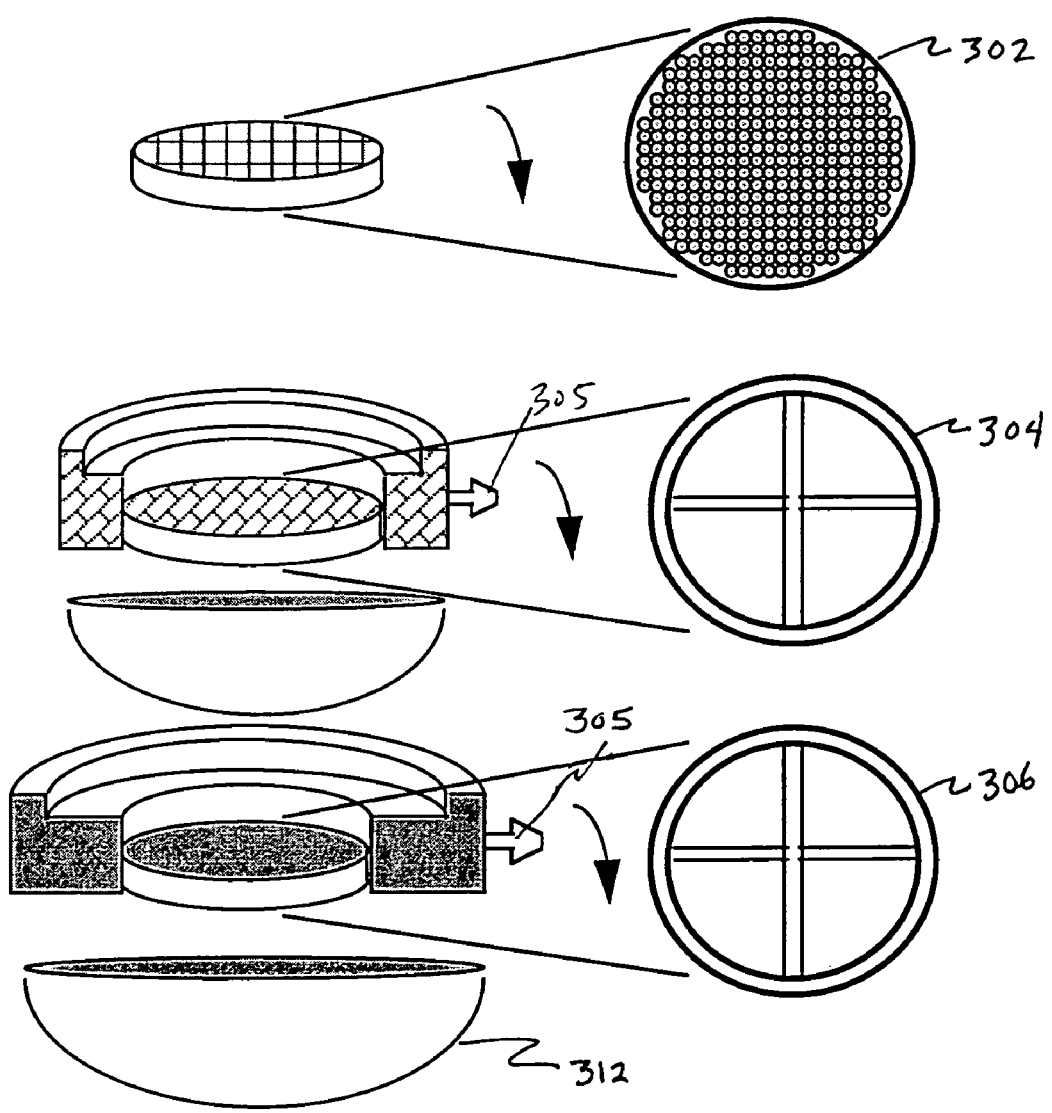

FIG. 3E provides an alternative illustration of the manifolds.

Figure 4:
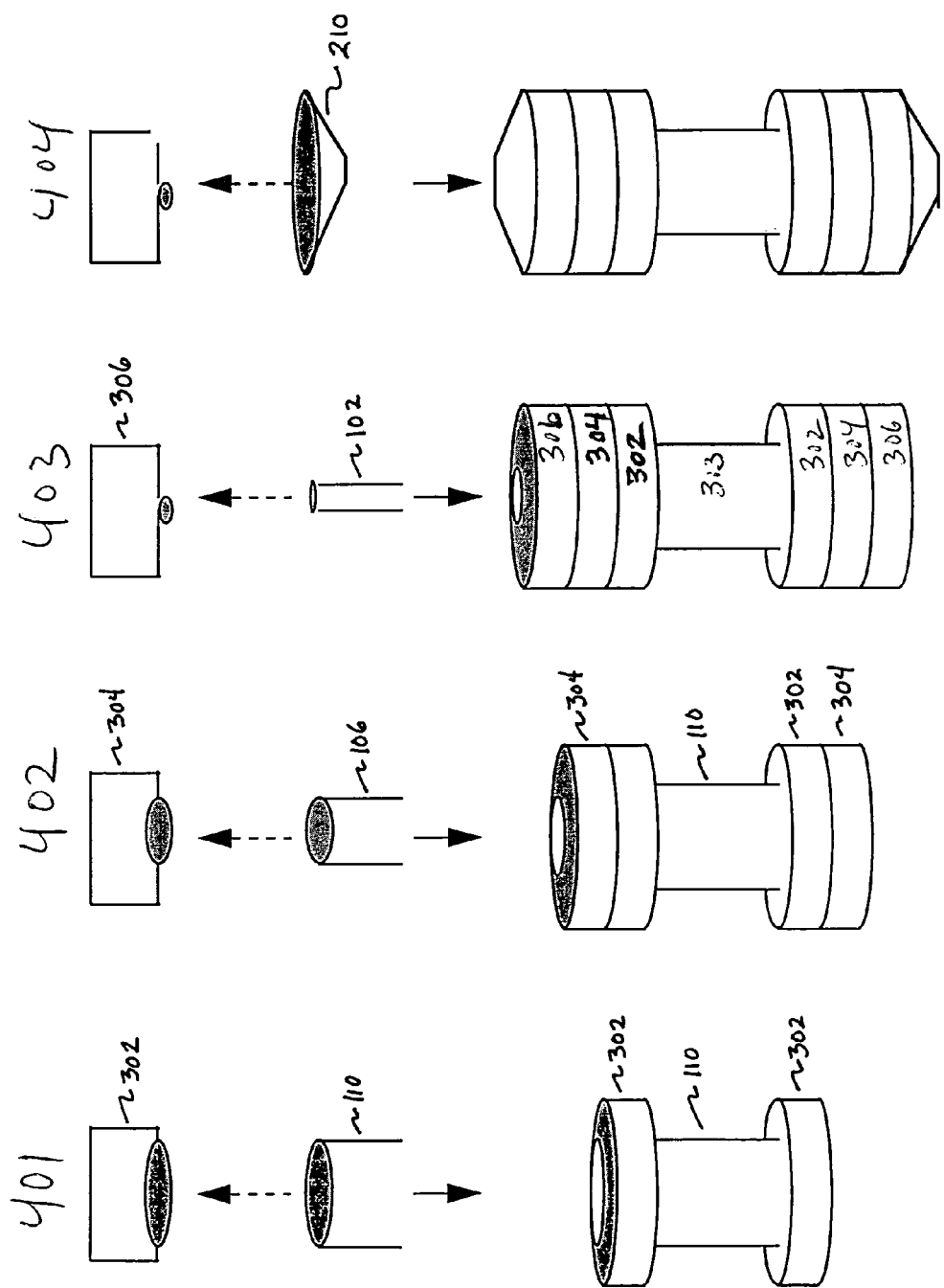

FIG. 4 illustrates the four main steps for two procedures used to construct multicoaxial bioreactors.

Figure 5:
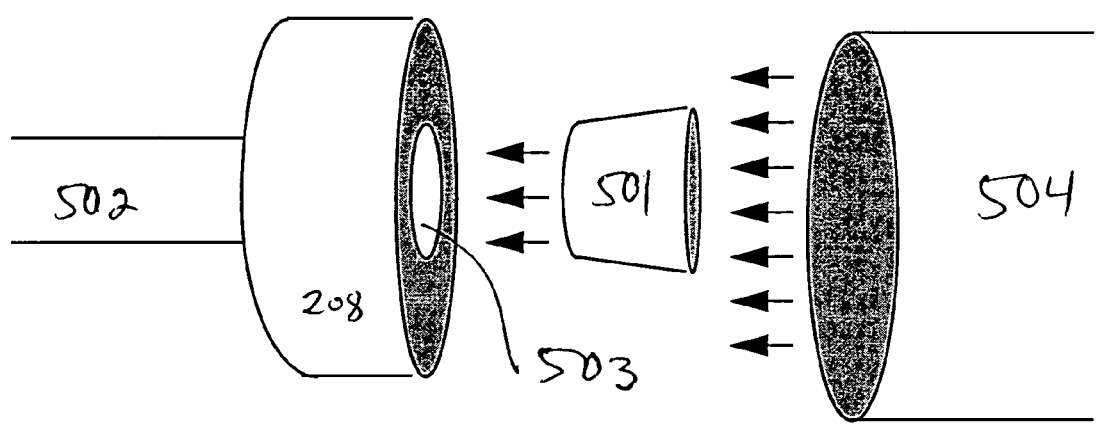

FIG. 5 illustrates a general process of thermoplastic welding hollow fibers.

Figure 6A:
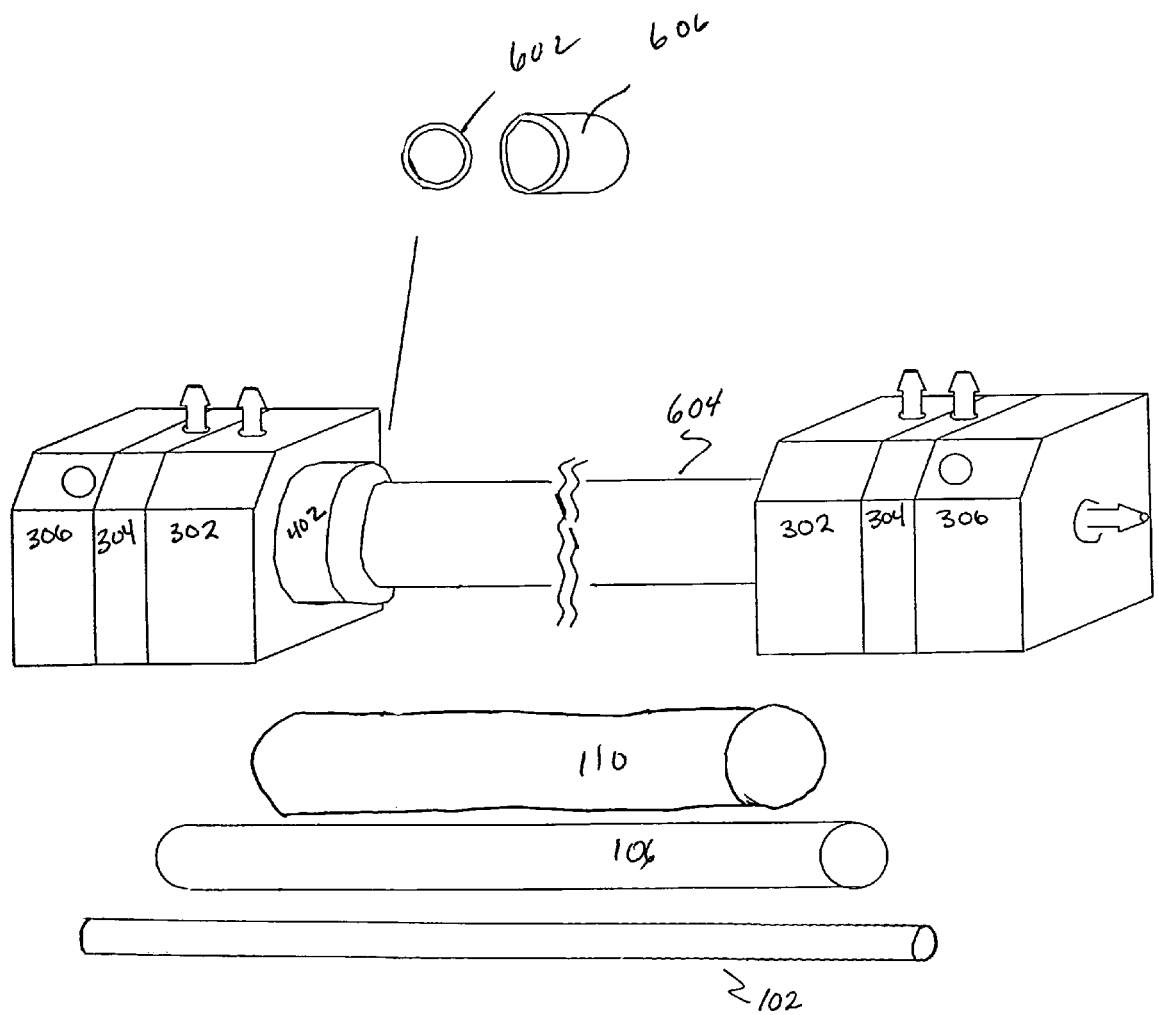

FIG. 6A illustrates a perspective view of a two sided embodiment of a bioreactor.

FIG. 6B illustrates a detail of the front side of the first manifold.

FIG. 6C illustrates a detail of the back side of the first manifold.

FIG. 6D illustrates an exploded view of the first manifold and associated elements.

FIG. 6E illustrates detail of the front side of the second manifold.

FIG. 6F illustrates a detail of the front side of the second manifold.

FIG. 6G illustrates a detail of the back side of the second manifold.

Figure 6H:
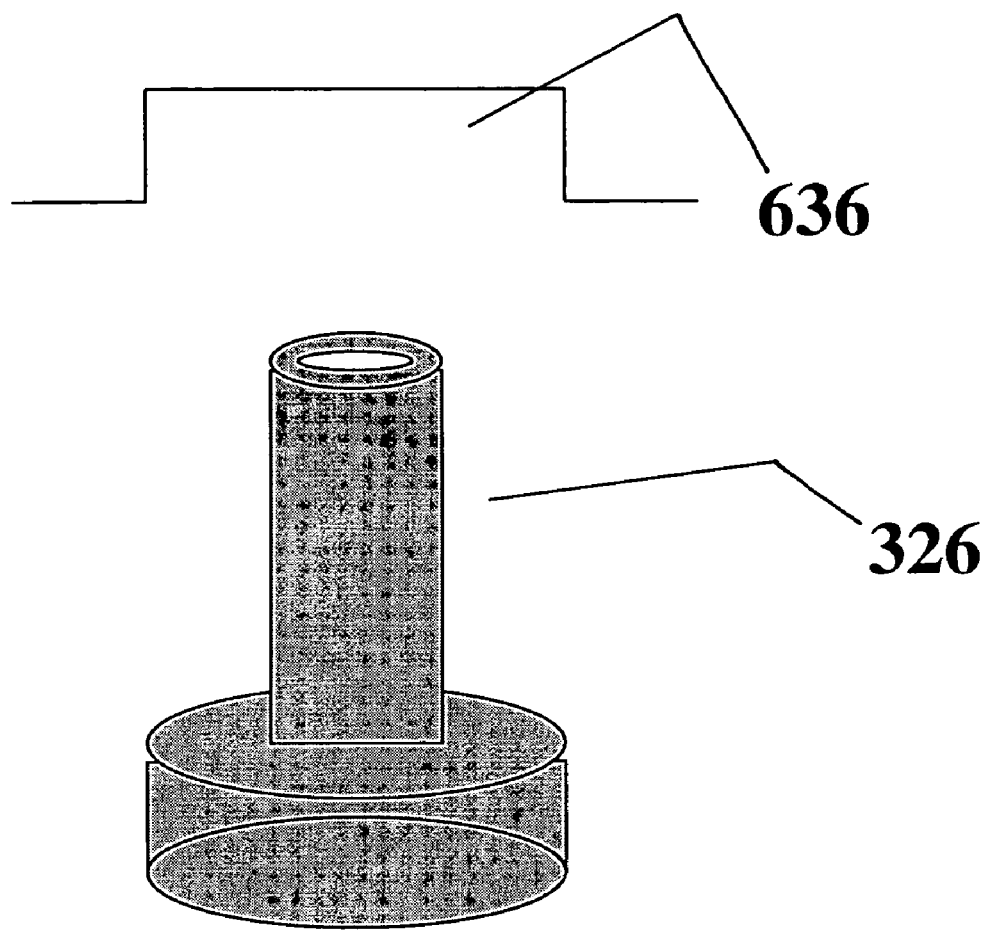

FIG. 6H illustrates a collar and a detail of the manifold.

Figure 6I:
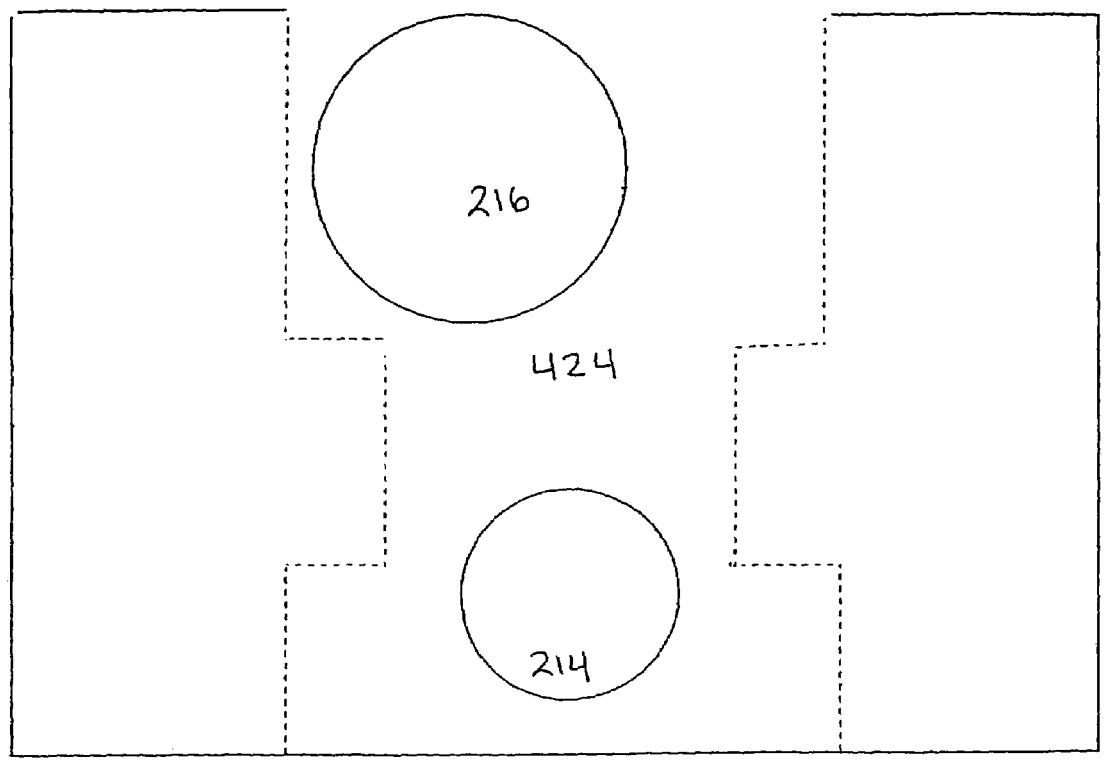

FIG. 6I is a cross-section of the second manifold.

FIG. 6J illustrates a detail of the front-side of the third manifold.

FIG. 6K illustrates a front perspective of the third manifold.

FIG. 6L illustrates a back view of the third manifold.

FIG. 6M illustrates a cross-section of the second and third manifolds.

Figure 6N:
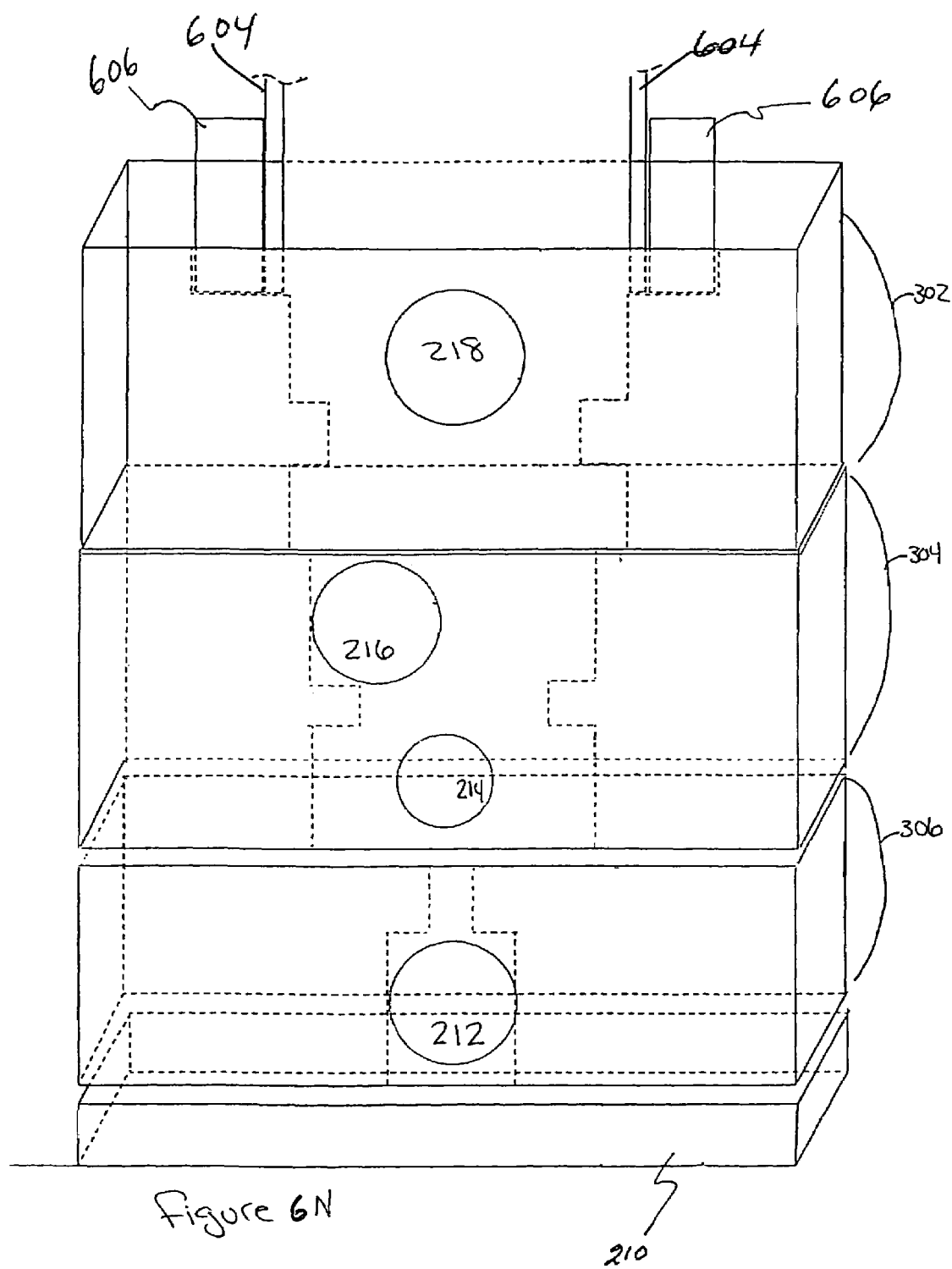

FIG. 6N provides a plan view of the complete assembly of a two sided bioreactor.

Figure 7:
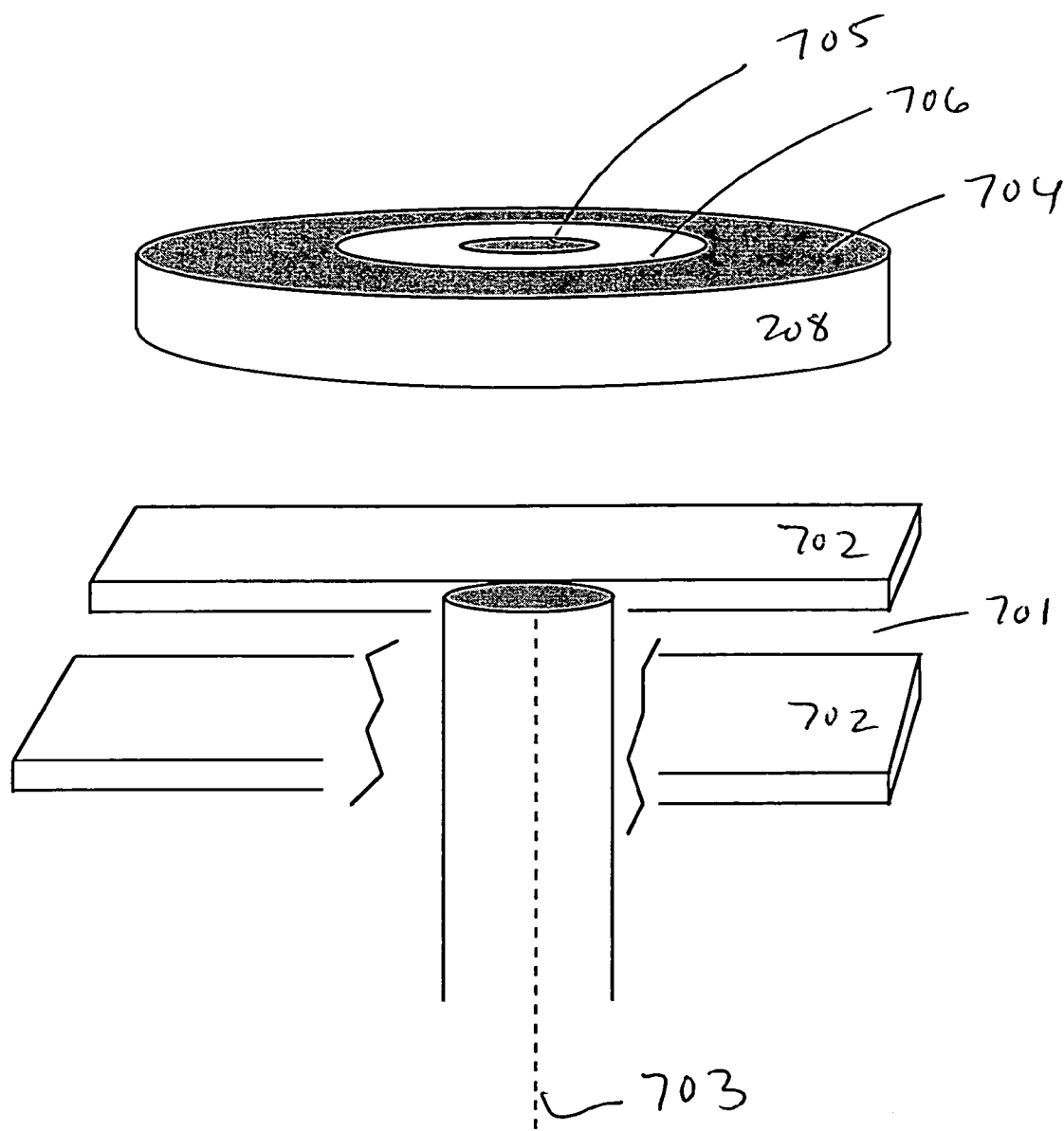

FIG. 7 illustrates a stand for mass producing bioreactors.

Figure 8:
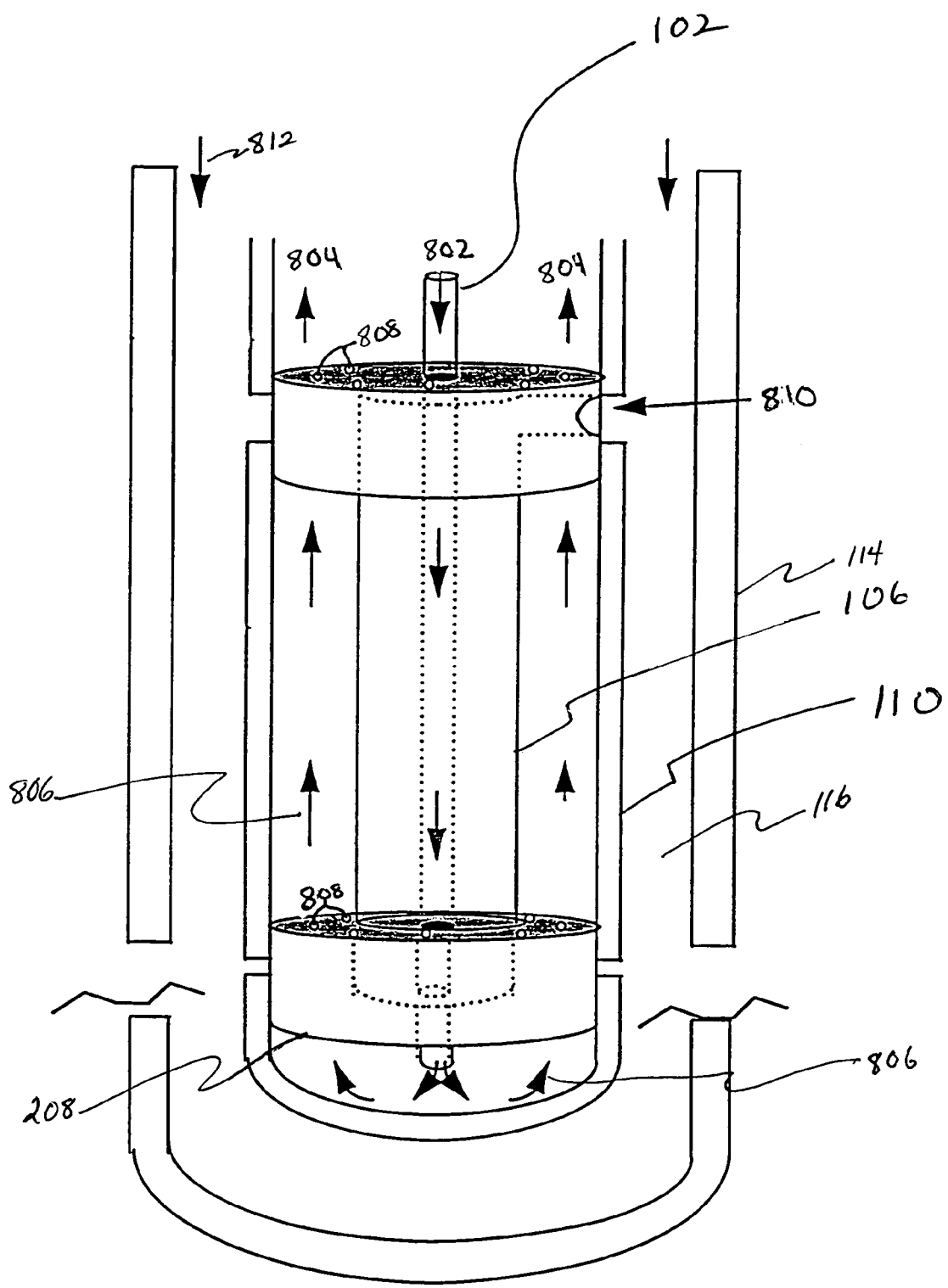

FIG. 8 illustrates a perspective view of a one sided bioreactor.

Figure 9:
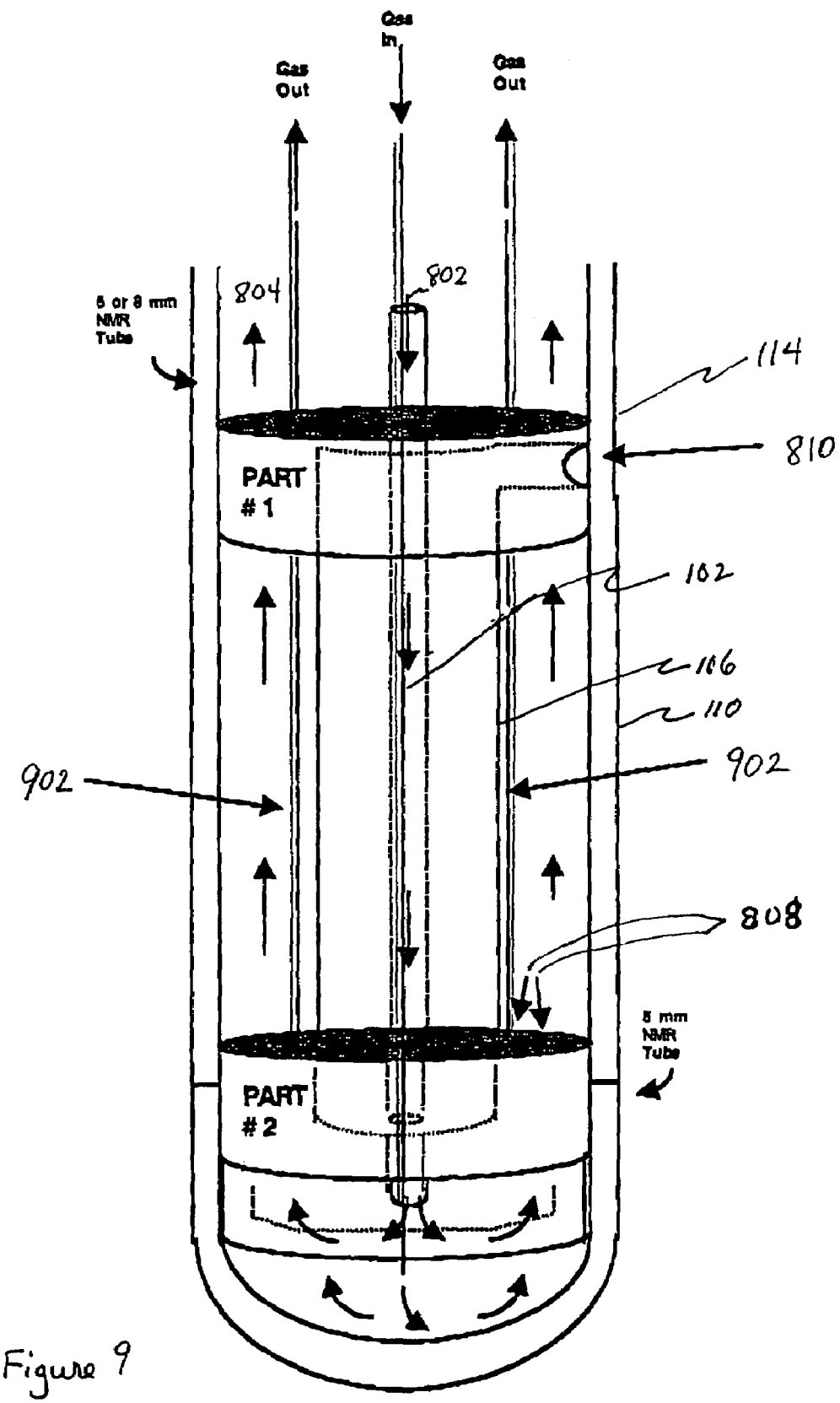

FIG. 9 illustrates a small one-sided bioreactor with integral oxygenation.

Figures 10A, 10B, 10C:
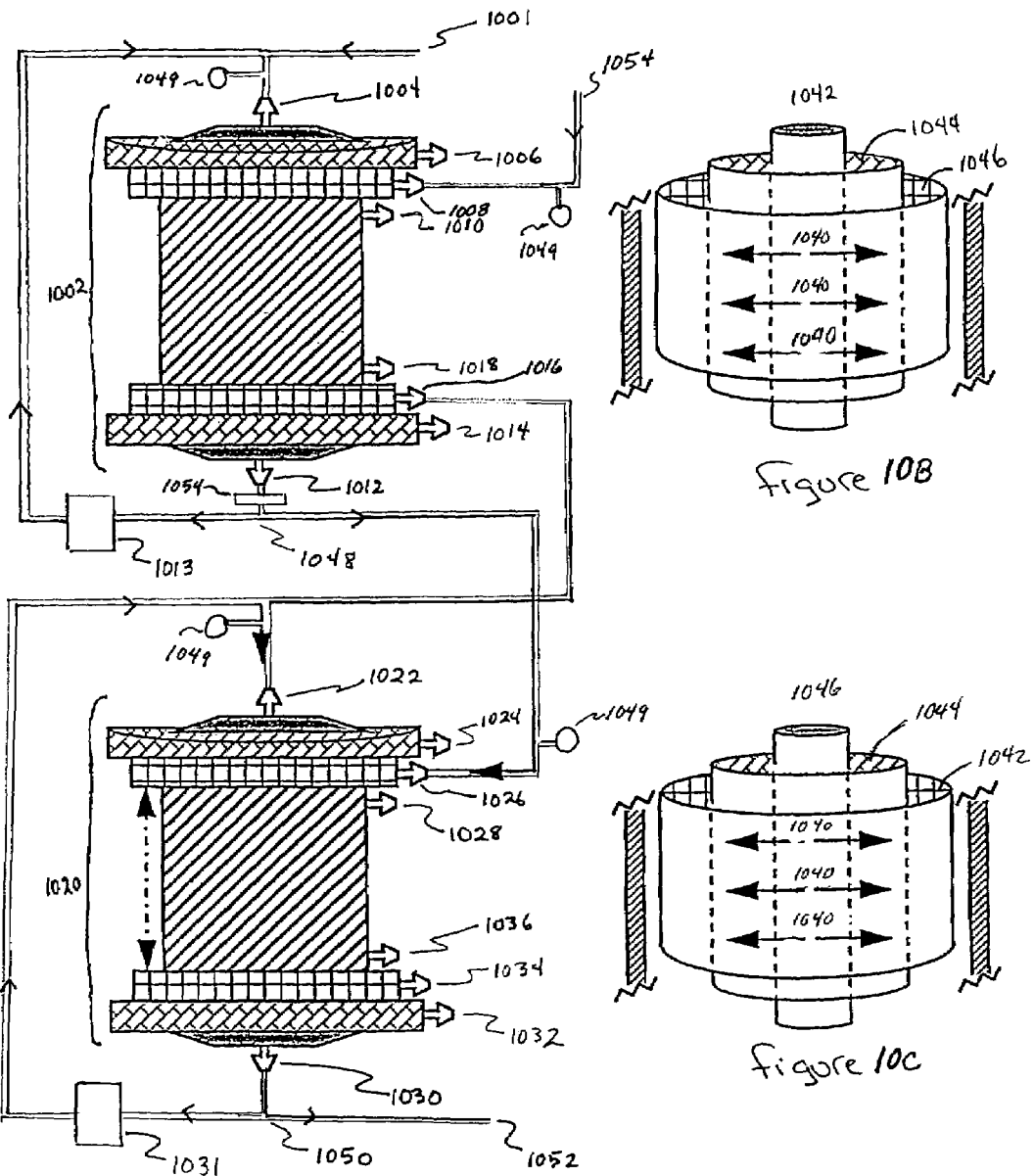

FIG. 10A further illustrates a serially linked bioreactor with an elevation view.

FIG. 10B illustrates radial flow of the serially-linked bioartificial liver with a detail view.

FIG. 10C illustrates radial flow of the serially-linked bioartificial liver with a detail view.

Figure 11A:
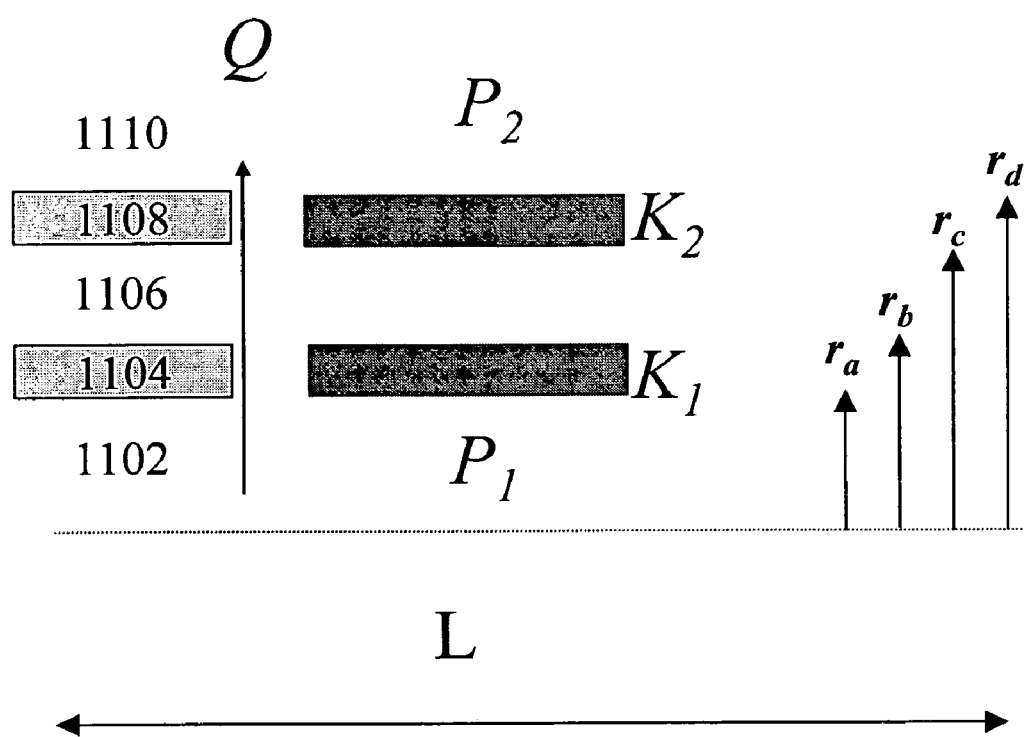

FIG. 11A illustrates the variables used in the implementation of Darcy's law.

Figure 11B:
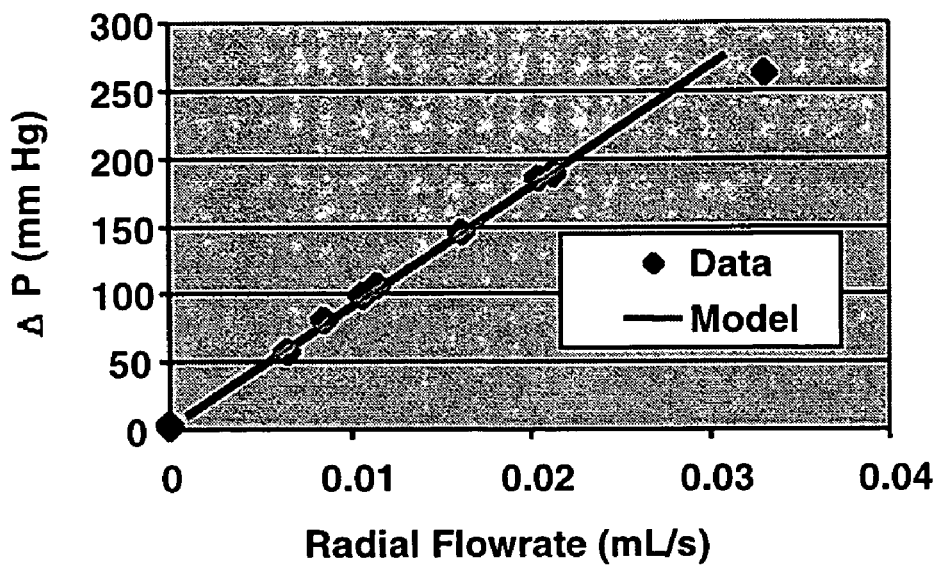

FIG. 11B illustrates a relationship between radial flow rate and a pressure differential.

Figure 11C:
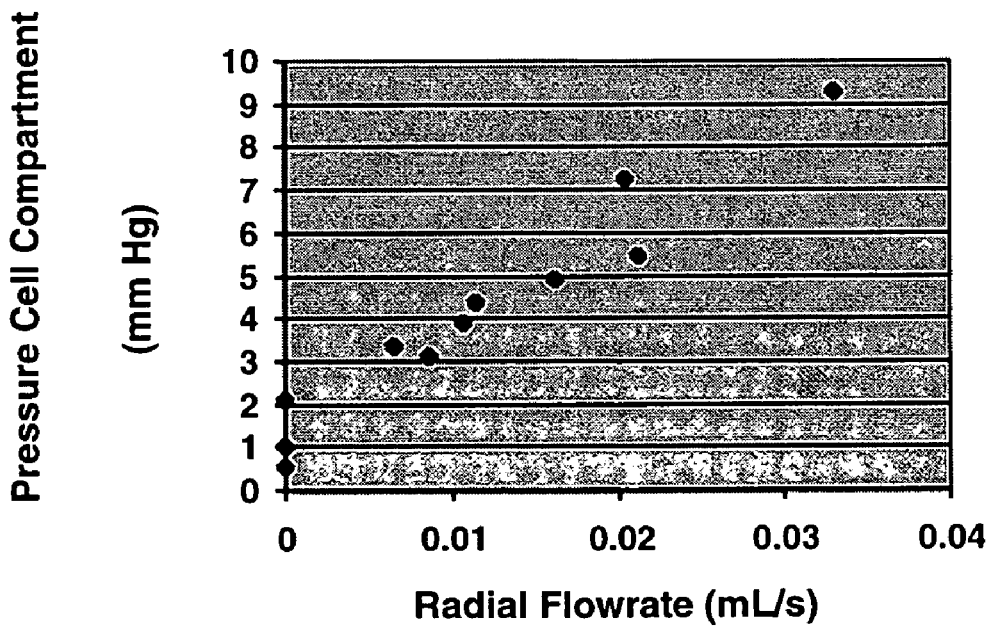

FIG. 11C illustrates a relationship between a radial flow rate and pressure in one cell compartment.

Figure 12:
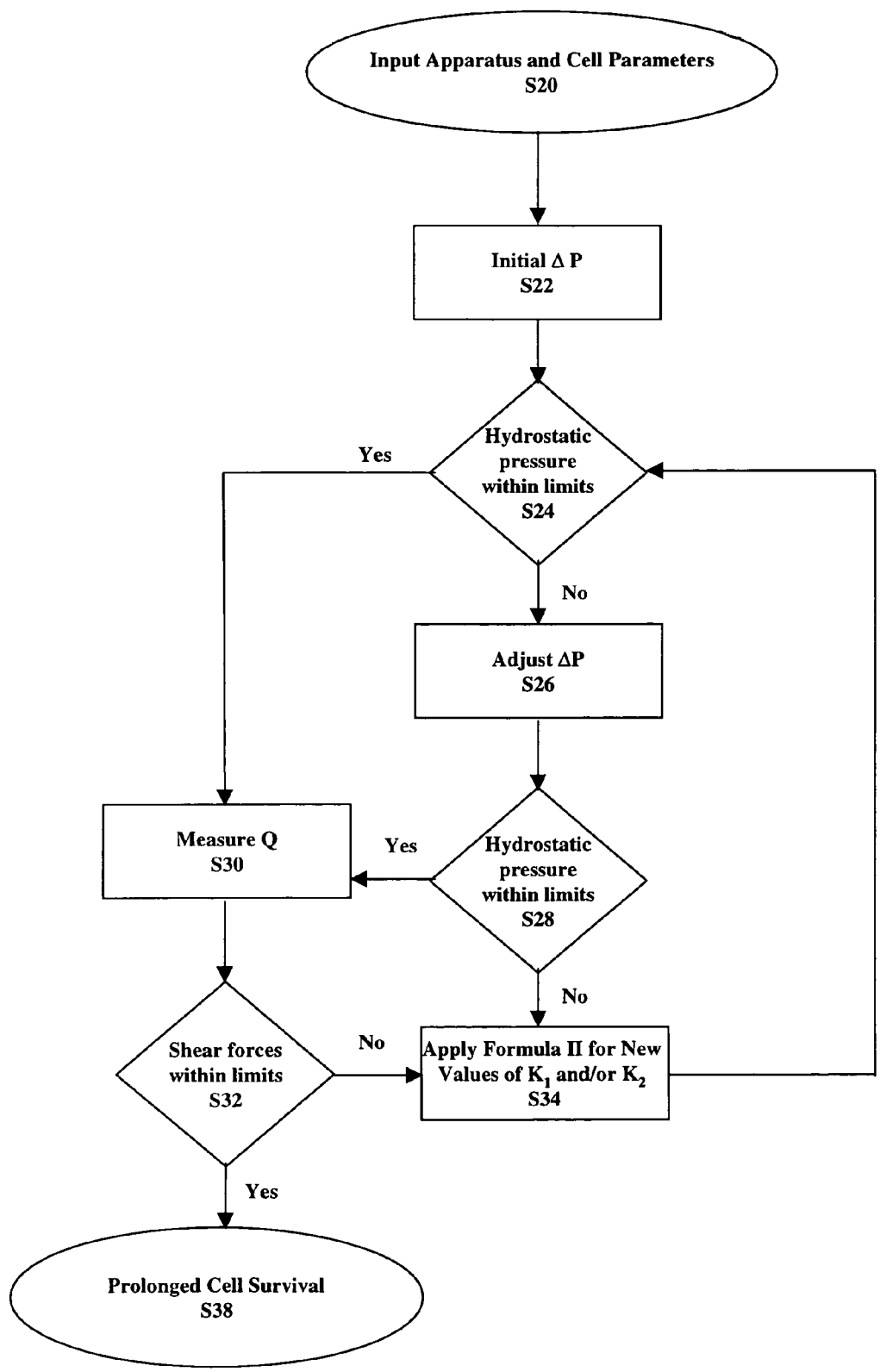

FIG. 12 illustrates the algorithm for the selection of hollow fiber characteristics for attaining superior physiological function and cell viability.

Figure 13A:
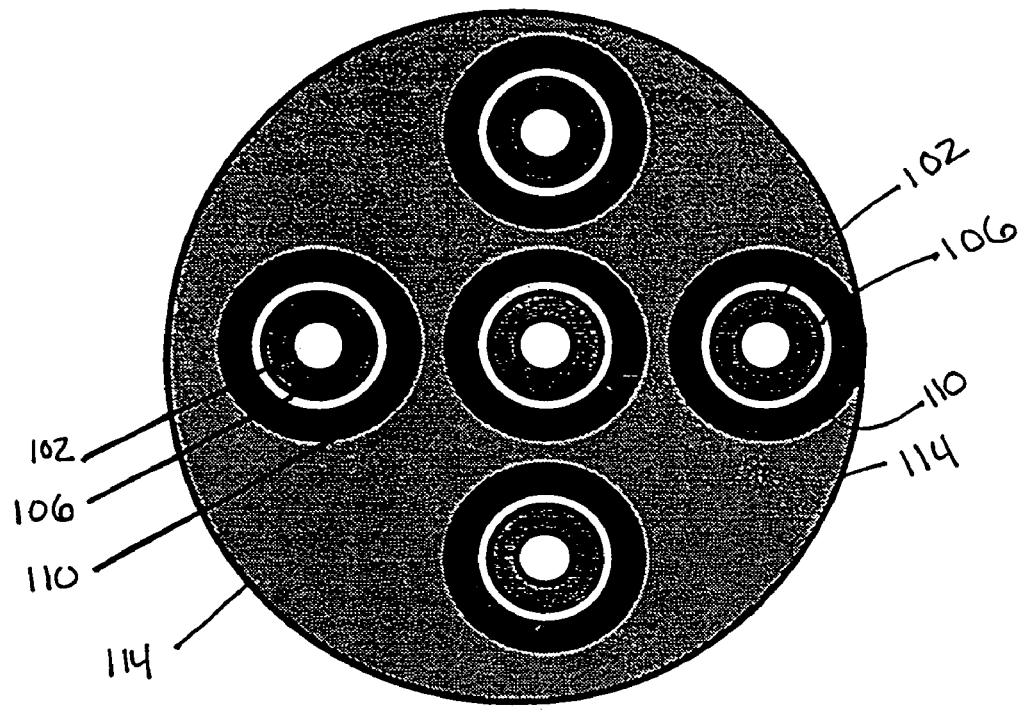

FIG. 13A illustrates a cross section of a multi-coaxial bioreactor.

Figure 13B:
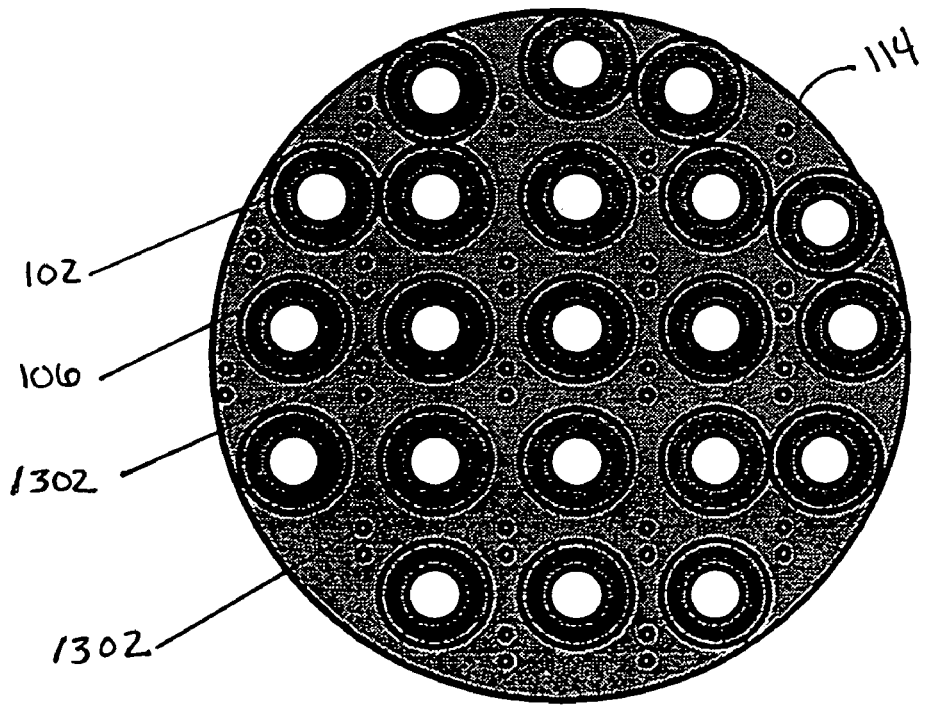

FIG. 13B illustrates a cross section of an alternative embodiment of a multi-coaxial bioreactor.

Figure 14:
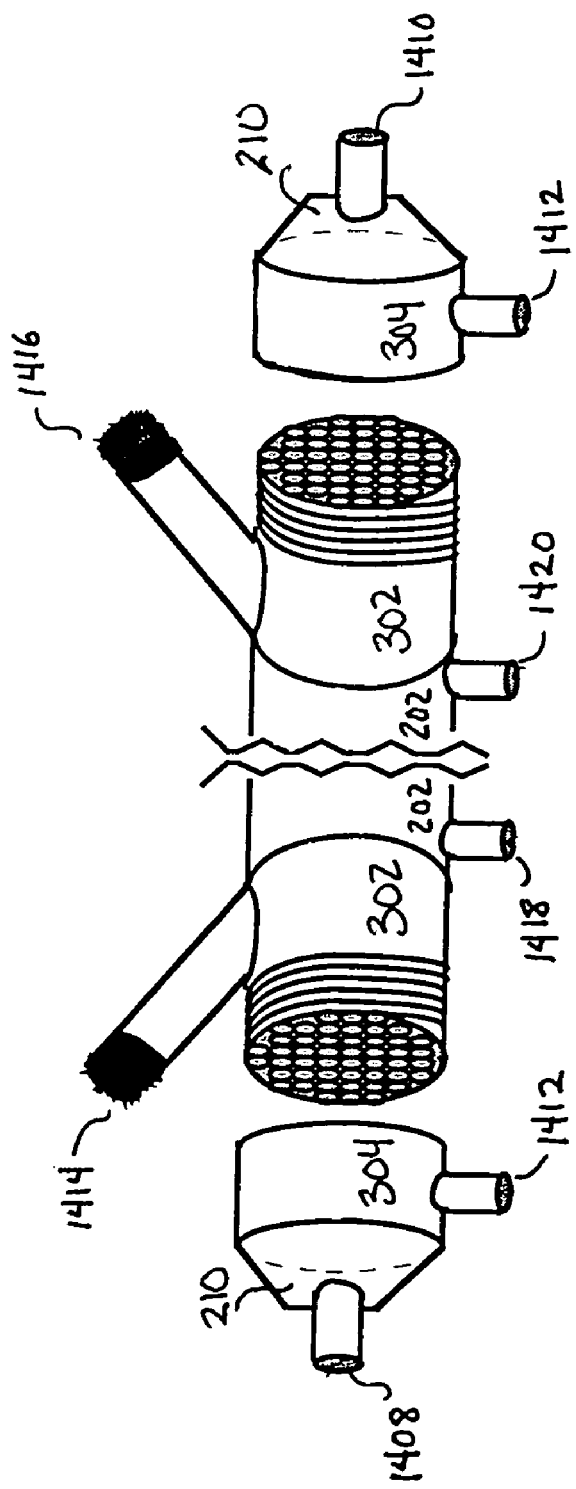

FIG. 14 illustrates perspective view of an embodiment of a bioreactor.

Figure 15:
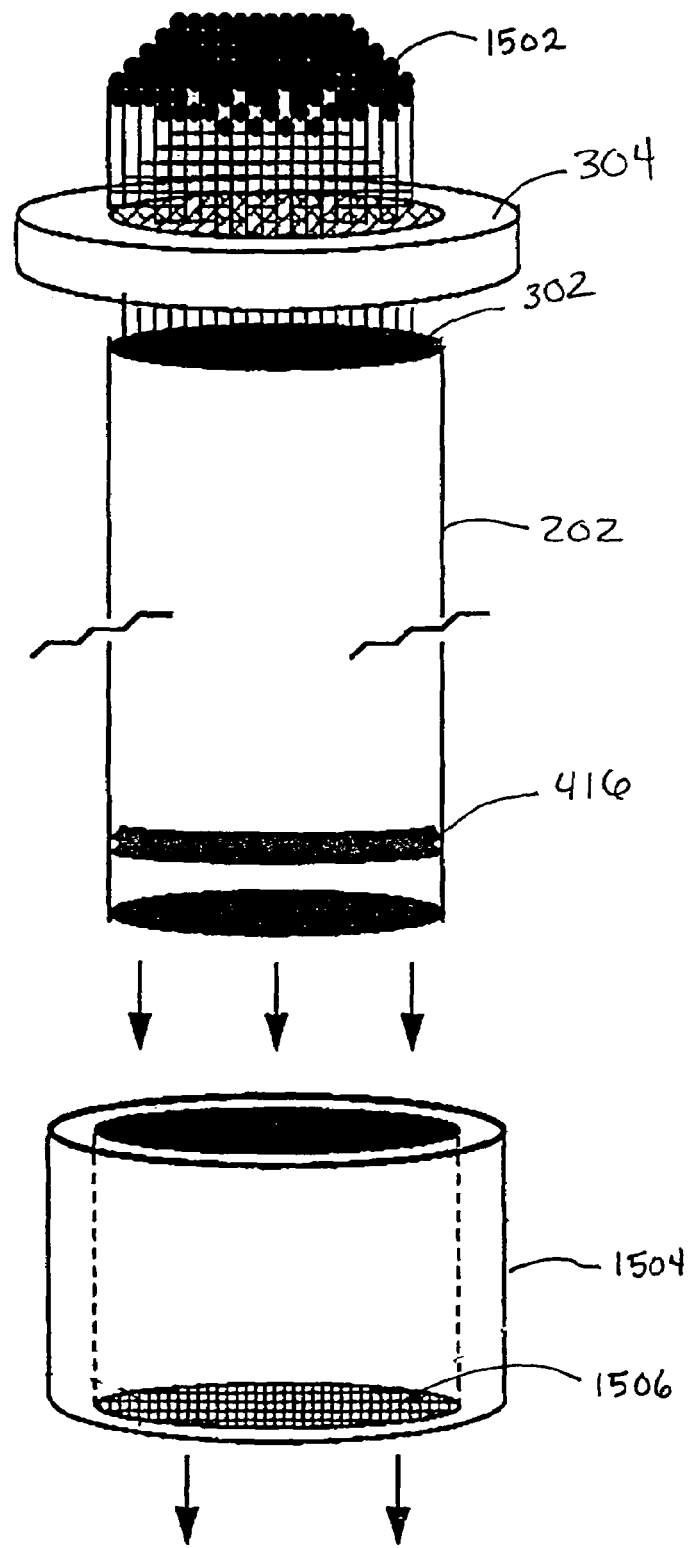

FIG. 15 illustrates a perspective view of a device used in the construction of a bioreactor.

5. DESCRIPTION OF THE PREFERRED EMBODIMENTS 5.1 Definitions

Annular space. The radial distance separating two adjacent hollow fibers.

BAL. Bioartificial liver. Also, specific embodiments of the present invention: the scaled-up multi-coaxial hollow fiber bioreactor, the tight packed hollow fiber bioreactor or the serially-linked bioreactor with a complement of liver cells, nutrient medium, and gases.

Bioreactor module. Coaxially-arranged semipermeable hollow fibers. One module forms the core of the multi-coaxial hollow fiber bioreactor whereas the scaled-up multi-coaxial hollow fiber bioreactor comprises many modules.

Biotransformation. The metabolic detoxification of blood or plasma by tissues or cells.

Fourth compartment. The compartment, if present, in a bioreactor embodiment that is bounded by the outside of the third hollow fiber and the inside of the fourth, that is, adjacent, hollow fiber, and is connected to two ports, the fourth compartment inlet port and the fourth compartment outlet port.

First compartment. The compartment in any of the bioreactor embodiments that is bounded in part by the inside of the first and innermost coaxial hollow fiber and is connected to two ports, the first compartment inlet port and the first compartment outlet port.

Integral aeration. Exposure to a gas, typically air or oxygen with carbon dioxide, at almost all points along a flow path. Integral aeration is distinguished from serial aeration, in which a bubbler or gas exchange device is inserted at one point in the fluid circuit.

Manifold. A part of the bioreactor located at an end of the fibers and intended to physically separate compartments and split flow of fluids.

Microfiber or microbore hollow fiber. A semipermeable hollow fiber of 200 to 500 micrometer o.d.

Multi-coaxial hollow fiber bioreactor. The bioreactor comprising three or more coaxially-arranged semi-permeable hollow fibers encased by a hollow housing.

Nutrient medium. The balanced electrolyte solutions enriched with sugars, trace minerals, vitamins, and growth enhancers. Each particular formulation is named by or for the formulator, sometimes with whimsical or non-illuminating designations. Nutrient media include, but are not limited to: RPMI 1640 (Roswell Park Memorial Institute, formulation #1640), Ham's F-12 (the twelfth formulation by Dr. Ham in his F series), DMEM (Dulbecco's modified Eagle's medium), and CMRL-1415 (Connaught Medical Research Laboratory formulation #1415). Nutrient media are routinely enhanced by addition of hormones, minerals, and factors known to those of ordinary skill in the art, including, but in no way limited to, insulin, selenium, transferrin, serum, and plasma.

One-sided multi-coaxial hollow fiber bioreactor. The version of the multi-coaxial hollow fiber bioreactor that has both inlet and outlet ports on the same end plate. This version is particularly adapted to NMR studies and to studies where access to all ports from one side is necessary.

Outermost compartment. The compartment in any of the bioreactors that is bounded by the outside of the outermost hollow fibers and the inside of the housing, and is connected to two ports, the outermost compartment inlet port and the outermost compartment outlet port.

Potting. A term of the art meaning the joining of elements, as by gluing, or any other suitable means.

Scaled-up multi-coaxial hollow fiber bioreactor. The bioreactor comprising arrays of from about 20 modules to about 400 modules of coaxially-arranged semi-permeable hollow fibers, where the entire set of modules is encased by a hollow housing.

Second compartment. The compartment in a bioreactor embodiment that is bounded by the outside of the first and innermost coaxial hollow fiber and the inside of the second, that is, adjacent, coaxial hollow fiber, and is connected to two ports, the second compartment inlet port and the second compartment outlet port. In the one-sided multi-coaxial hollow fiber bioreactor and in some dead-ended fiber designs only one port provides access to compartment 2.

Serially-linked bioreactor. The system comprising a plurality of scaled-up multi-coaxial hollow fiber bioreactors or of tight-packed hollow fiber bioreactors, or a combination, in which two or more compartments are connected in a continuous and serial manner. In this context, each scaled-up bioreactor is referred to as a bioreactor subunit.

Third compartment. The compartment in any of the bioreactor embodiments that is bounded by the outside of the second hollow fiber and the inside of the third, that is, adjacent, coaxial hollow fiber, and is connected to two ports, the third compartment inlet port and the third compartment outlet port.

Tight-packed hollow fiber bioreactor. The scaled-up bioreactor comprising arrays of from about 20 modules to about 400 modules of coaxially-arranged semi-permeable hollow fibers. Microfibers for aeration are arranged parallel and adjacent to the modules and the whole encased by a hollow housing.

5.2 Elements of the Apparatus

The instant invention includes a modular multi-coaxial bioreactor, having in theory, no limit to the number of coaxial fibers. In a preferred embodiment a scaled-up multi-coaxial bioreactor comprises at least two sets of manifolds, at least three hollow fiber sizes, at least two sets of endcaps, and a housing. This embodiment of the bioreactor contains at least four separated compartments. The modular design is composed of two sets of manifolds, with each pair of manifolds connected to each end of the fibers. There is a series of about 20 to about 400 holes coaxially arranged across the sets of manifolds and coaxially aligning the fibers. The manifolds optionally include flow distributors so that fluid and gas phase flow rates through the fibers are approximately uniform. The fiber manifold assemblies are attached radially from the largest to the smallest diameter fibers, and axially from the smallest to the largest diameter fibers. Fibers with smaller diameter are inserted into fibers of larger diameter and the respective manifolds are sealed together. To align fibers, two or more dowels are inserted through precisely drilled holes in the three manifolds or by interconnecting tongue and grooves on adjacent manifolds.

The bioreactors of the current invention advantageously combine 'integral' oxygenation with defined diffusion distances, have ports to accommodate potential bile duct formation, and/or are easily scalable. Integral oxygenation permits efficient mass transfer of dissolved gases and control of pH. Defined diffusion distances permit predictable axial and radial physico-chemico-biological parameters such as shear forces, availability of nutrients, and pH. In use with patients, one or more of the at least four compartments can be used for patient blood plasma while another can be used to perfuse cells with integrally oxygenated media. Optionally, two or more bioreactor units are attachable in series so that toxins can perfuse out of plasma radially through the cell mass in one unit and infuse synthetic factors in the next unit. There is the potential for the biliary system to develop using the ports as the bile duct exit ports.

Figure 1A:
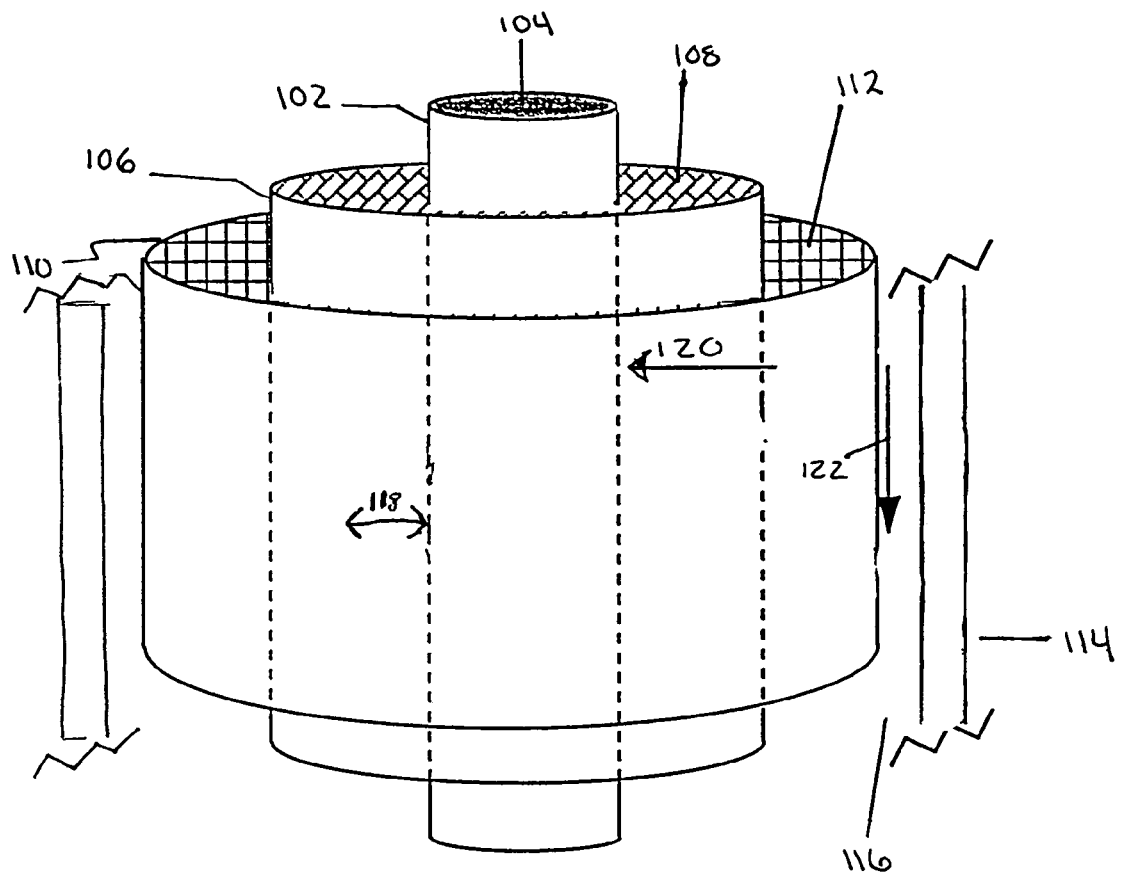
FIG. 1A illustrates a partial view of a multi-coaxial fiber unit comprising a plurality of compartments.

FIG. 1A illustrates a multi-coaxial fiber unit according to the instant invention comprising a plurality of compartments. Innermost fiber 102 provides intracapillary space or first compartment 104 for the receipt of standard media or plasma. Middle fiber 106 provides annular space or first middle compartment 108 for the containment of cells such as liver cells. Outer fiber 110 provides extracapillary space or second middle compartment 112 for the receipt of media. Housing 114 defines the outermost perimeter of the multi-coaxial fiber unit. Space or outermost compartment 116 between housing 114 and outer fiber 110 allows for the receipt of a gas. Diffusion distance 118 is half the width of first middle compartment 108. Radial perfusion 120 is the radial flow of, for example, dissolved oxygen through the fiber unit, while axial perfusion 122 is the axial flow of, for example, dissolved oxygen through the fiber unit.

Figure 1B:
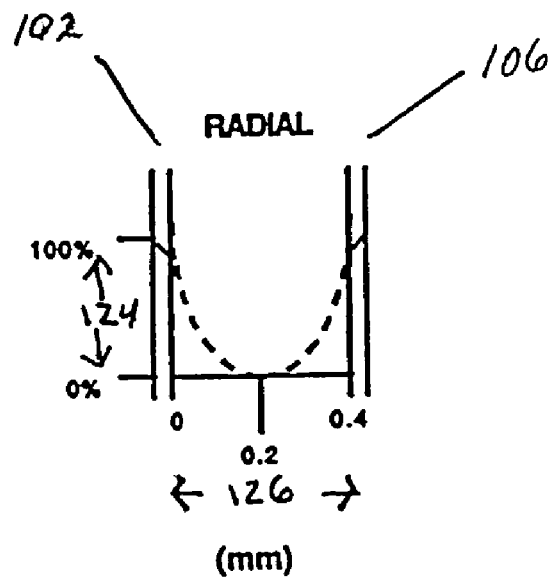
FIG. 1B illustrates a graphical representation of radial oxygen concentrations.

FIG. 1B shows a radial oxygen gradient across the first middle compartment 108 of a coaxial bioreactor having viable cells and integral oxygenation, where oxygen concentration is equal in the first compartment 104 and second middle compartment 112, and an annular space 126 of 0.4 mm (millimeters) separators 102 and 106. As shown, oxygen percentage 124 approaches zero as distance 126 approaches the diffusion distance 118 of 0.2 mm. As distance approaches 0.4 mm, percentage oxygen 124 approaches 100 percent, again due to oxygen diffusion from the second middle compartment 112.

Figure 1C:
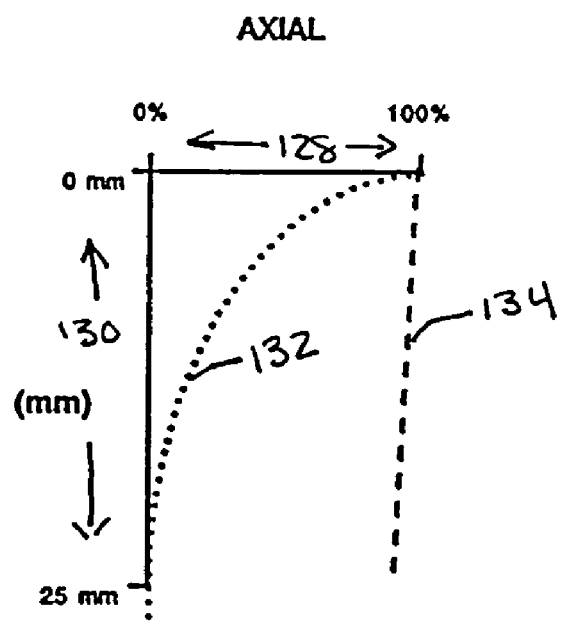
FIG. 1C illustrates a graphical representation of axial oxygen concentrations.

FIG. 1C shows axial oxygen gradients obtained through the use of bioartificial liver bioreactor designs having either "in-series" or "in-parallel" oxygenation. As shown, percentage of oxygen 128 decreases with distance 130 when "in series" 132 oxygenation is used, but remains nearly constant when "in parallel" 134 oxygenation is used, thereby demonstrating the decreased axial oxygen gradient due to integral oxygenation.

This invention permits precise control of desired diffusion distances in conjunction with integral oxygenation, and the modular design in conjunction with the potting material permits fibers of any composition to be arranged in a desired multi-coaxial order. Potting materials are known to those skilled in the art; such as that disclosed in U.S. Pat. No. 4,227,295 to Bodnar et al., which is herein incorporated by reference in its entirety. Where thermoplastic fibers are used, such as polypropylene, polyethylene, polysulfone, etc., then bioreactors can be constructed using a thermal bonding method such as described by Robinson in U.S. Pat. No. 5,015,585.

FIG. 2A illustrates a scaled-up multi-coaxial bioreactor comprising a plurality of multi-coaxial fiber units. In a preferred embodiment, the bioreactor comprises from about 20 to about 400 multi-coaxial fiber modules contained in housing 202. However, in theory, there is no limit to the number of coaxial fibers. As shown, housing 202 is 17 centimeters in length 204 with an 8 centimeter diameter 206, although alternative dimensions are envisioned. For example, the length of fibers can be from about 2 centimeters to about 50 centimeters and the diameter can be from about 1 centimeter to about 100 centimeters. Housing 202, for example, comprises three sets of manifolds 208, and one set of endcaps 210, one for each respective end of the bioreactor. One set of manifolds is needed for each size of hollow fiber. The housing is constructed of glass, polycarbonate, polypropylene, polyethylene, Delrin, Teflon, steel, brass, ceramic, or any other suitable material. Manifolds 208 and endcaps 210 can be machined or formed from acrylic, thermoplastic, ceramic, or any other suitable material. The hollow fibers comprising each multi-coaxial fiber module are preferably semi-permeable, and are in each of, for example, 3 sizes: approximately 5 millimeter outer diameter (o.d.) polysulfone; approximately 3 millimeter o.d. polysulfone; and approximately 1 millimeter o.d. cellulose acetate. There are thus three fibers per coaxial fiber unit, and three manifolds per module of fibers with the manifolds connected to each end of the fibers. The desired ΔP can also be created by restricting the effluent flow rate from port 212, for example by use of a needle valve. The invention also envisions embodiments having more than three coaxial fibers in each fiber module, with corresponding manifolds and ports.

Each bioreactor of the above listed or similar dimensions can support up to about 160 grams of tissue. Furthermore, in another embodiment a larger cell mass capacity is supported by using a larger annular compartment for the cell compartment and/or using longer fibers. An annular design for the cell compartment has an additional advantage over using single tubes because orders of magnitude greater biomass can be obtained. For example, a bioartificial liver described by Hu et al., U.S. Pat. No. 5,605,835 where hepatocytes are encapsulated in collagen in the innermost intracapillary compartment, would require 44,860 cellulose acetate hollow fibers of 200 micrometer diameter to attain the about 120 grams of tissue needed as an extracorporeal liver. In contrast, the embodiment of the present invention illustrated by FIG. 2 uses a factor of 150-fold fewer fibers.

Openings leading to ports allow for the movement of materials. Innermost ports 212 allow for the flow of media or plasma through the bioreactor. First middle ports 214 allow for the inoculation of cells into, or flow of cells through, the bioreactor. Second middle ports 216 allow for the flow of media through the bioreactor. Lastly, outermost ports 218 allow for the flow of gas through the bioreactor. Alternative uses of ports are also envisioned. For example, media can flow through ports 218, cells into, or through, ports 216, media or plasma through 214, and oxygen or other gases through 212.

FIG. 2B illustrates an enlarged view of a multi-coaxial fiber unit comprising a plurality of compartments located within the multi-coaxial bioreactor. As shown, media or plasma residing within first compartment 104 can either flow to or be received from innermost port 212. Similarly: (1) cells residing within first middle compartment 108 can either flow to, or be received from first middle port 214; (2) media located within second middle compartment 112 can either flow to, or be received from second middle port 216; and (3) gas residing within outermost compartment 116 can either flow to, or be received from outermost port 218. Also depicted is a module of hollow fibers consisting of innermost fiber 220, middle fiber 222 and outermost fiber 224. Embodiments comprising modules with more than one middle fiber are also envisioned.

FIG. 3A further illustrates a set of manifolds 208, including first manifold 302, second manifold 304, and third manifold 306. The manifolds each consist of a circular region about 15 centimeters in diameter, each with about 20 to about 400 holes, although any number of holes is possible. The holes are of three different diameters corresponding to the outer diameter of the respective fibers. This permits 20 fibers per row with a 2 mm space between holes, although optimum hole patterns are based on the number of desired fiber modules. These fibers can consist of any desired hollow fiber or tube with appropriate changes in the design specifications of the respective parts to fit the respective fiber diameters.

Two exemplary potting procedures are described: one that results in centered coaxial fibers, and one that does not. In both procedures the fibers are inserted into respective manifolds 208. The outer fiber 110 can be composed of any air permeable material such as, silicon, ceramic, glass, etc. As an example, polypropylene outer hollow fibers can be used in conjunction with thermoplastic welding.

The potting procedure used to center the fiber requires three additional sets of parts shown in FIGS. 3A, 3B and 3C: (1) first hollow fiber guide 314 for first manifold, second hollow fiber guide 316 for second manifold, and third hollow fiber guide 318 for third manifold, (2) spacers 320, and (3) hollow fibers clips (outer 322, middle, 324, and inner, 326) for each respective hollow fiber size (outer 110, middle 106, and inner 102). The hollow fiber guides can be composed of any material that can maintain rigidity at 3 mm thickness. The manifold and hollow fiber guide are placed against each other, sequential manifold holes are aligned with dowels, and outer fibers 110 are inserted through the holes of the manifold and then the hollow fiber guide with the ends of the fibers extending at least 1 cm beyond hollow fiber guide. The fibers are inserted in the housing 202 and the other end of the outer fibers are inserted into next first manifold 302 and first hollow fiber guide. The hollow fiber guide is extended away from manifold a distance permitting the pair of spacers 320 to slide between manifold and hollow fiber guide. The spacers 320 are glued on respective sides to adjacent manifold extensions 330. Once manifolds 208, spacer 320, and hollow fiber guide are secured, the hollow fibers are secured with tape or clips. Outer 322, middle 324, and inner 326 fiber clips that fit each fiber size are inserted across each row of fibers serving to keep fibers taut to maintain coaxiality and to pinch close the inner lumen so epoxy will not clog hollow fiber during potting. Therefore, fiber clips are varying lengths depending on row length. The secured fibers, spacer, and hollow fiber guide are inserted into a casting pot 312 which is screwed on or sealed to manifold 208 and serves to retains the epoxy during the potting process. The assembly is placed upright with casting pot 312 on the bottom and with a 10 to 45 degree downward tilt toward port 305 potting material, e.g., epoxy, is injected into side port 305 and runs down the side of the manifold 208 through holes 332 filling voids 334 contained by casting port 312. The bottom of the casting pot 312 is tapped to remove air bubbles. An appropriate amount of epoxy is added to fill voids 334 and to a level to cover both sides of manifold 308. Once the epoxy has nearly cured, the hollow fiber guide, spacer 320, casting pot 312, and epoxy is cut off leaving a very small layer of epoxy 308 over manifold. Therefore, the spacers 320, hollow fiber guides 314, 316, 318 and fiber clips 322, 324 and 326 serve two purposes: (1) they keep fibers taut and centered while potted, and (2) create a region for epoxy to cure between hollow fiber interstices that can be cut leaving a layer of epoxy 308 over manifolds 208.

Other methods can be used to center the inner fiber. In a first example, a rigid rod is inserted into the lumen of the inner fiber to center it. Then cells are mixed with a temperature-dependent gelling matrix, such as collagen, and the matrix is induced to gel. Then, the rod is removed. In a second example, a monofilament fiber with a diameter equal to the necessary inter-fiber spacing acts as a spacer. The monofilament made of polypropylene, polyethylene, or other appropriate material is helically wound around the inner fiber with one complete revolution every centimeter or so. The inner fiber with its monofilament winding is then inserted into the middle fiber. This permits the inner and middle fibers to be axisymetric. Therefore, the inoculated cells undergo a cork screw-type path. The monofilament is potted with the inner fiber using element 306.

FIG. 3D illustrates a cut out and enlarged view of a multi-coaxial fiber unit comprising a plurality of compartments located within the multi-coaxial bioreactor and formed by the centered coaxial fiber process. Thus, first manifold 302 is bound on the top and bottom by epoxy 308 and partially defines outermost compartment 116 and second middle port 216. Second manifold 304 is bound on the top and bottom by epoxy 308 and partially defines second middle port 216 and first middle port 214. Third manifold 306 is bound on the top and bottom by epoxy 308 and partially defines innermost port 212.

The potting process resulting in non-centered fibers does not require hollow fiber guides, monofilament, or spacers but requires a centrifuge. FIG. 3E is an illustration of three sets of manifolds 208, showing first manifold 302, second manifold 304, third manifold 306, and casting pot 312. Note the second manifold 304 and third manifold 306 do not have holes and will not coaxially align fibers. The epoxy potting process is described by Bodnar et al. (U.S. Pat. No. 4,227, 295) herein incorporated by reference in its entirety. This process involves inserting the fiber ends into the two respective manifolds. The fibers ends are gathered and then secured and sealed with tape, string, or some other material. Then, the casting pots 312 are attached to both ends. The assembly is attached to a centrifuge rotor at the axial center of the assembly. A small flat container is placed above the assembly, and has holes at each end which are attached to the ports 305 at each end of the assembly. As the centrifuge rotates, epoxy is placed in the middle of the container and is forced out toward the ends of the container, down the holes of the container, through the ports 305, and into the casting pots 312 filling the interstices of the fiber bundle. Once the appropriate amount of epoxy has flowed to the casting pots 312, the assembly continues to spin until the epoxy partially cures. Then the excess epoxy and casting pots 312 are cut away at both ends leaving open hollow fiber holes at both ends of the assembly, and the next epoxy potting step is performed. To insure that leaks do not occur between manifolds, the manifolds 208 are welded or epoxied along their borders.

FIG. 4 is an illustration describing the four main steps of both procedures for assembly of one module of the instant invention which is composed of three sets of fibers. The procedure is, first step 401 insert the outer fiber 110 ends into holes in first manifolds 302, then attach first manifold 302 to housing 202, and pot fiber ends. The next step 402 is insert second set of fibers, or middle fibers 106, into outer fiber 110, insert fiber ends in holes in the second manifolds 304, and pot fiber ends. The next step 403 is insert inner fibers 102 into middle fibers 106 and insert fiber ends into holes on the third manifolds 306 and pot fiber ends. The last step 404 is attach endcaps. At least two dowels are inserted into adjacent manifolds during the second 402 and third 403 steps by way of dowel holes 310 to align holes in adjacent manifolds. The second manifold 304 has four dowel holes 310 because at least 2 are filled with a hollow fiber that maintains dowel hole void 310 after potting process is complete so dowel can be inserted and second manifold 304 can be aligned properly with third manifold 306. Thermoplastic welding can be performed on similar materials, therefore, in the instant invention the first manifold 302 is made of polypropylene in order to weld polypropylene fibers.

FIG. 5 illustrates the general process of welding. A Teflon cork 501 is inserted in the inner diameter of the hollow fiber 502 forcing the fiber walls against the wall of the holes 503 in the manifold 208. A heat gun, or thermoplastic welder 504 is used to melt the fiber wall 502 and wall of the holes 503 together. Once the assembly is cooled the teflon plug is removed. A jib of teflon plugs that match the first manifold 302 holes is used to weld the outer fibers ends to the respective first manifolds 302. Both ends of the housing 313 have a slot into which first manifold 302 fits. A similar jib of teflon plugs fitting the second manifold 304 and third manifold 306 can be used to thermoplastically weld all three sets of fibers if fibers are composed of same material as manifold, and most likely will result in non-centered coaxial fibers. In the first step 401, first manifold 302 is welded to housing 313. In second step 402, second manifold 304 is welded to manifold 302. In third step 403, third manifold 306 is welded to second manifold 304. In fourth step 404, endcaps 210 are welded to third manifold 306.

FIG. 6A illustrates a two-sided multi-coaxial hollow fiber bioreactor. The bioreactor is assembled using parts machined or formed from polypropylene or any other machined or formed material using two of each part, one for each respective end of the bioreactor, three semi-permeable hollow fibers, and an approximately eight to ten millimeter diameter nuclear magnetic resonance (NMR) tube (available, for example, from Wilmad Inc., Buena, N.J.). The hollow fibers used to construct the bioreactor are approximately 8 millimeters o.d. with wall thickness of 0.5 millimeters, 2.6 millimeters o.d. with wall thickness of 0.4 millimeters, and 0.8 millimeters o.d. with wall thickness of 0.2 millimeters and made of polypropylene with 0.2 micrometer pore size (available, for example from Akzo-Nobel, Germany). The respective fibers can be composed of a 8 millimeter o.d. silicone tube (available, for example, from Dow Corning, Midland, Mich.), and 3 and 1.3 millimeter o.d. polysulfone hollow fibers (available, for example, from AG/Technologies, Inc., Wilmington, Del.) with 0.4 and 0.2 millimeter wall thickness, respectively, and with 0.1 and 0.65 micrometer pore sizes, respectively. Alternatively, a smaller o.d. and thinner walled silicone tube can be used for the outer fiber 110 and pulled over a perforated rigid tube to give structural rigidity. Diffusion of oxygen is inversely proportional to the wall thickness, and therefore, the thinner walled silicone tubing will permit superior mass transfer of oxygen. The 2.6 millimeters o.d. polypropylene fiber can be replaced and constructed with a 3 millimeters o.d. polysulfone fiber with a wall thickness of 0.5 millimeters and with 0.65 micrometer pore size. These fibers can consist of any desired hollow fiber or tube with appropriate changes in the design specification of the respective parts to fit the respective fiber. Fibers are cut to be at least 2 millimeters longer than their final length when assembled.

The outer fiber 110 can be coated with a perfluorinated polymer to bridge or clog the pores to avoid 'wetting', or saturation with water, or pores and effectively eliminating evaporation of water from media using a process provided by Compact Membrane Systems (Wilmington, Del.) or other similar pore-filling process. Coating could also be performed on the scaled-up multicoaxial bioreactor described in FIG. 3. For mass transfer purposes, the coating occurs on the media sided of the fiber. If coating is not performed the air compartment must have higher pressure than adjacent media compartment to avoid pore wetting, and the gas stream should be warmer than media stream to decrease evaporation and condensation.

In the instant invention, the two-sided multi-coaxial bioreactor is assembled with largest outer fiber 110 (e.g., 5 millimeters i.d., 8.1 millimeters o.d.) and first manifold 302. Securing means such as polyurethane epoxy or thermoplastic welding or combination thereof are used to fix the fibers to the respective parts. Housing, an NMR tube 604, is secured to first manifolds 302 by collars 606 and O-rings 602.

FIGS. 6B, 6C and 6D further illustrate the first manifold. As shown in FIG. 6B, the front side comprises first circular recessed area 610 while as shown in FIG. 6C the back side comprises first circular raised area 612. Both first circular recessed area 610 and first circular raised area 612 partially define first void 614. As shown in FIG. 6D, O-ring 602 is placed into first circular recessed area 610. Collar 606 is attached thereto. Outermost port 218 is also shown.

FIGS. 6E, 6F, 6G and 6H further illustrate the second manifold. As shown in FIG. 6F, the front side comprises second circular recessed area 620 while, as shown in FIG. 6G, the back side comprises second circular raised area 622. Both second circular recessed area 620 and second circular raised area 622 partially define second void 624. In order to insure that cells do not collect in the space between second manifold 302 and third manifold 304, a collar 326 can be slipped over the middle fiber 106 and snuggly fitting into the second void 624 and into the front void 636 of third manifold 304. Second middle port 216 is also shown. FIG. 6C also illustrates the fashion in which first manifold 302 communicates with second manifold 304.

FIG. 6I provides a perspective view of the second manifold, illustrating second void 624, second middle port 216, and first middle port 214.

FIGS. 6J, 6K and 6L further illustrate the third manifold. As shown in FIGS. 6J and 6K, the front side comprises third circular recessed area 630 that partially defines third void 634. First middle port 214 is also shown in FIG. 6L. FIG. 6M also illustrates a cross section of the complete assembly, showing how second manifold 304 communicates with third manifold 306.

FIG. 6N is a top view of the complete assembly of a two sided bioreactor with all four inlet and outlet ports on one side of the manifold, illustrating first manifold 302, second manifold 304, third manifold 306, media port 212, cell port 214, media port 216, gas port 218 and collar 606.

The bioreactor can be mass produced using stand or holder 702 illustrated in FIG. 7. The stand holds the manifold 208 and fiber axis 703 in a groove 701 so that the axis of the fiber 703 is 90 degrees perpendicular to the plane of the manifold 704 containing the fiber hole opening 705. Then the fibers are fixed by filling the manifold/fiber space 706 with epoxy, or a thermoplastic welding process as depicted in FIG. 5. If epoxy is used then the epoxy is rapidly cured in an oven and then the other side is potted and the entire procedure depicted in FIG. 7 is repeated. The manufacture can be automated for mass production where the process of bioreactor assembly shown in FIG. 4 is performed robotically. In a mass produced two-sided bioreactor, the O-rings 602 and collars 610, and threads on first manifold 302 which are used to make a seal with the 10 mm glass NMR tube 604 are replaced by using a tube composed of polypropylene or appropriate material to replace the glass 10 mm NMR tube 604 and are thermoplastically welded or epoxied to create a seal. In a preferred embodiment the outer fiber 110 is welded and the two inner fibers 102 and 106 are epoxied. With respect to the coaxial fibers, the fiber manifold 208 assemblies (FIG. 6) are attached radially from the largest to smallest diameter fibers, and axially from the smallest to largest diameter fibers. The outer fiber 110 is inserted into 2 O-rings 602, 2 collars 606, a 10 mm NMR tube 604, and then into the first manifold 302. The two collars are tightened, and then first manifolds 302 at both ends of the bioreactor assembly are inserted into the grooves 701 of the stand 702. The outer fibers 110 are thermoplastically welded in place using, for example, the process described in FIG. 5. The bioreactor now assuming a dumbbell shape is ready for attaching the second manifold 304.

A second fiber of about 2.6 millimeter o.d. polypropylene or 3 millimeter o.d. polysulfone is inserted into the outer fiber of dimension 5 mm o.d. and affixed to second manifold 304 by the epoxy process depicted in FIG. 7. First manifold 302 and second manifold 304 are welded along their borders. A third fiber of 0.8 millimeter o.d. is inserted into the second fiber of 1.8 millimeter i.d. polypropylene or 2 millimeter i.d. polysulfone hollow fibers and is affixed to third manifold 306 as described above. During attachment of fibers to the manifold on only the second end of the bioreactor, the fibers are cut flush with their respective manifolds or part numbers. Endcap 210, or threaded hose bard, is glued to, or screwed onto third manifold 306 at each end.

FIG. 8 discloses a coaxial bioreactor with inlet port 802 and outlet ports 804 on one side of the bioreactor. In a preferred embodiment, this bioreactor is axially less than 40 millimeters long and the fibers are secured with manifolds or endcaps that have coaxial counter-sunk holes that fit the fiber diameters within ±5 mils of an inch. Optionally, hepatocytes center the inner fiber, thereby making construction easier and permitting axial scale-up. The bioreactor can be partially filled depending on inoculation procedure. The bioreactor is assembled with an inner fiber 102, middle fiber 106, outer fiber 110, and manifolds 208 in a fashion similar to the two-sided multi-coaxial hollow fiber bioreactor, except there is only one inlet and one outlet. The one sided multi-coaxial bioreactor of FIG. 8 uses the same fibers and NMR tube described above for the two-sided multi-coaxial hollow fiber bioreactor. In this embodiment housing 114 is an NMR tube. The specific design can be inserted in an 10 millimeter NMR probe used with conventional vertical bore magnets. Flow direction 806 can be switched by swapping inlet port 802 and outlet ports 804. The flow rate in the outer annulus is partly controlled by the diameter and number of holes 808 aligned as a circle around the three manifolds. The manifolds and fibers are assembled as described above for the two-sided single multi-coaxial hollow fiber bioreactor. Also shown is inoculation port 810 and air flow 812.

An additional one-sided multi-coaxial hollow fiber bioreactor design can be constructed by dead-ending the inner fiber 102 and omitting the holes 808 in the bottom manifold 812. This changes the flow configuration by forcing the flow path from inner compartment 104 through the first middle compartment 108 where cells reside and exiting through the second middle compartment 112, or vice versa. Since oxygenation occurs in the outer compartment in the instant invention, it is preferred to flow from second middle compartment 112 toward the inner compartment 104 so that media becomes appropriately oxygenated before entering the cell mass.

To enhance NMR sensitivity the one-sided bioreactor can be made to fit inside a smaller diameter NMR tube such as 8 to 15 mm. In order to achieve a smaller diameter, in one embodiment of the instant invention a 200 $\mu$m to 500 $\mu$m o.d. microbore aeration fiber serves as inner fiber 102, a 1 to 1.3 millimeter o.d., middle fiber 106, and a 3 to 4 millimeter o.d. outer fiber 110. With oxygenation occurring by way of the inner compartment 104 the preferred flow is from the first middle compartment 108, through cell mass in the second middle compartment 112, and exiting by way of the outer compartment 116. The gas chamber, of inner compartment 104, is dead-ended, and gas is flushed from the compartments by way of diffusion to a flowing air stream connected to the gas chamber by way of a tee connectors at the top of the bioreactor. In order to have air circulate through the bioreactor, an air flow-through the design is needed. The inner fiber 102 in FIG. 9 is manifolded at the bottom of the bioreactor and at least one 200 $\mu$m to 500 $\mu$m return microbore aeration fiber 902 is epoxied into holes 808 in the manifolds bordering the outer compartment 116 and used for media return. Alternatively, a two-fiber coaxial bioreactor is constructed from an inner fiber mini-oxygenator composed of 0.8 mm polypropylene fibers is placed in-line to the one-sided bioreactor and gas is heated by water-jackets to avoid outgasing due to temperature changes and/or differences between oxygenation device and bioreactor.

FIG. 10A illustrates the serially-linked bioartificial liver. It includes at least two bioartificial liver subunits with potentially up to about 160 g of tissue per subunit. Cell suspensions are introduced into the respective annular compartments by way of ports 1006 and/or 1014 and 1024 and/or 1032, and allowed to anchor to the annular compartments. Radial flow dynamics are used to perfuse media from plasma to cells for biotransformatory functions. The flow scheme is switched in the second subunit so synthetic factors can flow from the cells back into the plasma. Radial flow is discussed further, infra.

As shown in FIG. 10A, plasma 1001 from the patient enters first bioartificial liver subunit 1002 through first plasma entrance port 1004, media enters 1054 first bioartificial liver subunit 1002 through first media entrance port 1008 and gas enters first bioartificial liver subunit 1002 through first gas entrance port 1010. Radial flow is produced by selecting hollow fibers with characteristics of pore size and pore number such that the hydraulic permeability of the fiber is relatively high and by having a substantial pressure gradient across the fibers as determined in the hydrodynamic model discussed below. FIG. 10B depicts plasma flow under conditions where plasma compartment 1042 has higher pressure than cell compartment 1044 and media compartment 1046. Under these conditions, some plasma flows radially from entrance port 1004 to plasma compartment 1042, through cell mass contained in cell compartment 1044, into media compartment 1046, and out the media exit port 1016. The remaining plasma then exits first bioartificial liver subunit 1002 through first plasma exit port 1012, and the plasma is divided by tee-junction 1048. Media exits first bioartificial liver subunit 1002 through first media exit port 1016 and gas exits first bioartificial liver subunit 1002 through first gas exit port 1018. The elevated pressure in plasma compartment 1042 necessary to create the $\Delta P$ to drive radial flow is created by dividing the plasma stream at tee junction 1048 and rapidly recirculating plasma through plasma compartment 1042 by way of recirculating pump 1013 connecting the plasma entrance port 1004 to plasma exit port 1012. The flow rates or velocities create sufficient head pressure at the plasma entrance port 1004 and pump rates are adjusted for desired $\Delta P$ which is measured by pressure gauges 1048 at ports 1004 and 1008. The desired $\Delta P$ can also be created by insertion of a needle valve 1054 in the line between the plasma exit port 1012 and the tee junction 1048. In this manner, plasma flow rate can remain constant through the first bioartificial liver subunit 1002 and the desired $\Delta P$ is achieved by modulating flow through the needle valve. The same principle can be used to control radial flow in the second bioartificial liver subunit 1020. In an alternative embodiment, plasma compartment 1042 is dead-ended by eliminating plasma exit port 1012.

The flow scheme is then switched in the second subunit such that the fluid from exit port 1016 enters second bioartificial liver subunit 1020 through second media entrance port 1022, plasma enters second bioartificial liver subunit 1020 through second plasma entrance port 1026 and gas enters second bioartificial liver subunit 1020 through second gas entrance port 1028. A portion of the media flows radially from the entrance port 1022 through the annular cell layer and into the plasma component. The remaining media then exits second bioartificial liver subunit 1020 through second media exit port 1030 and the fluid stream is split at tee junction 1050 and a portion is returned to the patient 1052. Cells optionally exit second bioartificial liver subunit 1020 through second cell exit port 1032, plasma exits second bioartificial liver subunit 1020 through second plasma exit port 1034 and gas exits second bioartificial liver subunit 1002 through second gas exit port 1036. FIG. 10C depicts plasma-containing media flow where the media compartment 1046 is now switched with the plasma compartment 1042. As described above, the $\Delta P$ is established in the media compartment 1046 by rapid recirculation of the plasma-containing media by pump 1031 to create sufficient head pressure. The $\Delta P$ is measured by pressure gauges 1049 at ports 1022 and 1026. In an alternative embodiment, sufficient head pressure is created by eliminating or restricting (using a needle valve or other similar device) the flow through the second media exit port 1030.

In order to create radial flow, several flow configurations are possible. Flow rate differences in two compartments results in a pressure difference ($\Delta P$) creating radial flow across the annular space, which is governed by Darcy's law:

$$v_r = k \, \Delta P / \eta L \qquad (\text{I})$$

where $v_r$ is the radial flow velocity, k is the hydraulic permeability, a constant dependent on the physical features of the hollow fiber (including pore size and pore number), the solvent, and the solute, $\eta$ is the viscosity of the solution, and L is the length of the contact between the two compartments, here, essentially the fiber length. Any of a variety of pore sizes can be selected, including, but not limited to $10^{-6}$ m, $0.1 \times 10^{-6}$ m, and $0.05 \times 10^{-6}$ m. Thus radial flow can be enhanced by a suitable choice of fibers with a high hydraulic permeability and by modulation of flow rates.

A model based on Darcy's law permits one to estimate the correlation between pressure difference and radial flow given the hydraulic permeabilities of the inner fiber 102 and middle fiber 106. The model assumes incompressible and Newtonian fluid, and that the axial pressure gradient is negligible, and the flow rate across the fibers was constant. Deriving this equation for two concentric hollow fibers the following relationship is obtained.

$$\Delta P = \frac{Q}{2\pi L}\left[\frac{\ln\!\left(\frac{r_b}{r_a}\right)}{K_1} - \frac{\ln\!\left(\frac{r_d}{r_c}\right)}{K_2}\right] \qquad (\text{II})$$

FIG. 11A defines the variables used in the equation. Q is radial flow rate from compartment 1102 characterized by a hydrostatic pressure $P_1$, through pores in fiber 1104 characterized by hydraulic permeability $K_1$, through intermediate compartment 1106, then through pores in second fiber 1108 characterized by hydraulic permeability $K_2$ to compartment 1110 characterized by hydrostatic pressure $P_2$. The radial distances from a centerline to the inside of fiber 1104 is $r_a$, to the outside fiber 1104 is $r_b$, to the inside fiber 1108 is $r_c$ and to the outside of fiber 1108 is $r_d$. It is to be understood that the direction of radial flow of any particular chemical constituent, including but not limited to oxygen, culture medium, plasma, and biosynthetic products, depends on the direction of the pressure differential. The directions of flow and of the corresponding radial flow rate can be either positive or negative, and are represented by the sign of the flow and of Q. The invention contemplates values of Q corresponding to flow from inner compartments to outer compartments, and equally contemplates values of Q corresponding to flow from outer compartments to inner compartments. FIG. 11B compares the experimental data of radial flow from the second middle compartment 112 to the inner compartment 104 as a function of pressure difference to the modeled data using experimentally determined values of $K_1$ and $K_2$. FIG. 11C illustrates the pressure in the cell compartment 1106 corresponding to the experiment shown in FIG. 11B. Comparison of FIGS. 11B to 11C shows that the majority of transmembrane pressure difference occurs across the middle fiber 106 and this is because of the relatively large hydraulic permeability and wall thickness of the middle fiber 106. Therefore, cells are protected from the adverse effects of high pressure created in the second middle compartment 112, and as the hydraulic permeability of the middle fiber 106 increases, the pressure is more easily transmitted to the first middle compartment 108 and cells becomes less protected from the pressure in the second middle compartment 112. Therefore, this model can be generally used in the operation of the bioreactor to predict the appropriate pressure difference for given inner 102 and middle 106 fibers hydraulic permeabilities. In preferred embodiment, the device includes a software program based on this predictive model which aids in the selection of culture conditions regarding radial flow velocities and hydrostatic pressures in the cell compartment.

A method of selecting a radial flow rate in a bioreactor comprising semi-permeable fibers to enhance cell viability comprising: measuring a first hydraulic pressure associated with a first semi-permeable fiber and a second hydraulic pressure associated with a second semi-permeable fiber to obtain a pressure differential and adjusting the first hydraulic pressure, the second hydraulic pressure, or a combination thereof to select one or more radial flow rates so as to improve cell viability.

Thus, in one embodiment, the invention comprises a method of selecting a radial flow rate in a bioreactor comprising semi-permeable fibers to enhance cell viability comprising: measuring a first hydraulic pressure associated with a first semi-permeable fiber and a second hydraulic pressure associated with a second semi-permeable fiber to obtain a pressure differential and adjusting the first hydraulic pressure, the second hydraulic pressure, or a combination thereof to select one or more radial flow rates so as to improve cell viability. The first fiber and the second fiber can be coaxial. In a particular embodiment, the method of selecting a radial flow rate comprises selecting the radial flow rate based on the formula:

$$\Delta P = \frac{Q}{2\pi L}\left[\frac{\ln\left(\frac{r_b}{r_a}\right)}{K_1} - \frac{\ln\left(\frac{r_d}{r_c}\right)}{K_2}\right] \quad \text{(II)}$$

where $\Delta P$ is the pressure differential, Q is the radial flow rate, L is the length of the shorter of the first and second fiber lengths, $r_a$ is the radial distance from the centerline of the bioreactor to the inner surface of the first fiber, $r_b$ is the radial distance from the centerline of the bioreactor to the outer surface of the first fiber, $r_c$ is the radial distance from the centerline of the bioreactor to the inner surface of the second fiber, $r_d$ is the radial distance from the centerline of the bioreactor to the outer surface of the second fiber, $K_1$ is the hydraulic permeability of the first fiber, and $K_2$ is the hydraulic permeability of the second fiber.

The software can be in the form of an algorithm as illustrated in FIG. 12, and used to select mass transfer conditions for specific cell types. Initial $\Delta P$ values are obtained from a knowledge of characteristics of the bioreactor, including diffusion distance 118 and fiber length, as well as known physiological conditions in the tissue of interest.

A detailed description of the radial flow algorithm is provided in FIG. 12. The first step shown in block S20 begins with input of parameters of the bioreactor, including the geometry and dimensions of the bioreactor, and parameters of the cells, including resistance to hydrostatic pressures and shear stress. The pressure differential is then sampled, block S22. The next step requires a determination of whether the pressure differential is within the limits of hydrostatic pressure consistent with continued viability of the cells used in the system, as shown in block S24. If the pressure differential is not within permissible limits, the pressure differential is adjusted, as shown in block S26. Then the hydrostatic pressure is again measured to determine if it is within permissible limits, as shown in block S28.

If the determination from either block S24 or block S28 is that the hydrostatic pressure is compatible with cell viability, then the radial flow is measured, as shown in block S30.

The next step requires a determination of whether the shear forces associated with radial flow are within viability limits for the cell type of interest, as shown in block S32. If the shear forces are not within permissible limits, the formula II, supra, relating $\Delta P$ and the radial flow rate Q is applied, as illustrated in block S34. As a result of the calculation of block S34, more suitable hydraulic permeability $K_1$ and/or hydraulic permeability $K_2$ is determined, as necessary S36.

Upon change in one or more hydraulic permeabilities, as in block S34, the system returns to block S24 for further evaluation of first hydrostatic pressure and then shear force.

When the hydrostatic pressure is within limits consistent with cell viability, as in either block S24 or block S28, then the radial flow rate, Q, is measured as in block S30. If the shear forces associated with the radial flow is consistent with cell viability, then conditions for cell survival are established, as illustrated in block S38. By setting suitably narrow limits for permissible hydrostatic pressure and shear force, an optimum condition for prolonged cell survival is attained.

In another embodiment, the invention can comprise a computer readable medium including instructions therein for calculating a radial flow rate in a bioreactor comprising semi-permeable fibers, said instructions including the steps of: (a) receiving measurements of hydraulic permeability for each of at least two semi-permeable fibers, (b) receiving hydraulic pressure measurements associated with a pressure differential for at least two coaxial semi-permeable fibers, and (c) estimating said radial flow rate between said coaxial semi-permeable fibers.

FIG. 13A illustrates a cross section of a multi-coaxial bioreactor comprising three coaxial hollow fibers nested within each other. FIG. 13A depicts innermost fiber 102, middle fiber 106, outer fiber 110 and housing 114.

FIG. 13B illustrates a cross section of an alternative embodiment of a multi-coaxial bioreactor. FIG. 13B depicts innermost fiber 102 middle fiber 106, smaller aeration fiber 1302 and housing 114. Smaller standard aeration fiber 1302 is placed in the spaces formed by stacking coaxial fibers which comprise innermost fiber 102 and middle fiber 106. Thus, a first compartment is formed by the inner wall of innermost fiber 102. A second compartment is defined by the outer wall of innermost fiber 102 and the inner wall of middle fiber 106. A third compartment is defined by the outer wall of middle fiber 106 and housing 114. A fourth compartment is formed by the inner wall of smaller aeration fibers 1302. In alternative embodiments, a fifth compartment can be created for aeration purposes by inserting a fourth, small aeration fiber inside innermost fiber 102.

FIG. 14 illustrates an embodiment of a bioreactor. The following components are shown: first manifold 302, second manifold 304, endcap 210, inner compartment inlet 1408, inner compartment outlet 1410, cell compartment 1412, gas inlet 1414, gas outlet 1416, outermost compartment inlet 1418, outermost compartment outlet 1420 and housing 202.

FIG. 15 illustrates a device used in the construction of a bioreactor. Components shown include plurality of fibers 1502, second manifold 304, first manifold 302, housing 202, O-ring 416, vacuum head 1504, and mesh 1506. The vacuum allows for rapid insertion of smaller fibers into larger fibers. Mesh 1506 retains the fibers in place.

In scaled-up versions of the multi-coaxial bioreactor, manifolds consist of multiple coaxial holes for the various fibers, and dowels are placed in holes precisely located on the manifolds to insure that all multi-fiber units are coaxial. Since multi-fiber units are reproduced accurately due to the coaxial design, experimental parameters from a single multi-fiber unit are directly applied to the scaled-up bioreactor.

The construction of the bioreactor may have many variations that will be evident to the practitioner. As one example, the hollow fibers may vary in pore size, length, wall thickness and composition and the hydrodynamic model shown above and in FIG. 11 can be used to determine the optimum hollow fiber characteristics. The hollow fibers may be made of any of a number of materials including, but by no means limited to polysulfone, cellulose acetate, mixed esters of cellulose, regenerated cellulose, polyvinylalcohol, polyurethane, polyvinylidine, polypropylene, polycarbonate, and polyamide. Cellulose acetate is more permeable to nutrient media and polypropylene is more permeable to gases and those skilled in the art will select appropriate fibers based on these and other properties. The means of formation of pores and control of the pore size will be obvious to one of skill in the art and may include, but in no way be limited to, neutron bombardment, controlled polymerization, and incorporation of leachable agents. Any of several adhesives including polyurethane epoxy may be used for potting the fibers, and those skilled in the art will know of appropriate adhesives.

6. EXAMPLES

The following specific examples are provided to better assist the reader in the various aspects of practicing the present invention. As these specific examples are merely illustrative, nothing in the following descriptions should be construed as limiting the invention in any way. Such limitations are, or course, defined solely by the accompanying claims.

6.1 NMR Analysis of Liver Cell Function in the One-Sided Multi-Coaxial Hollow Fiber Bioreactor.

Sprague-Dawley rats are anesthetized with pentobarbital (50 mg/kg intraperitoneally). The liver is exposed by a ventral midline incision and the portal vein is cannulated for infusion of cell dissociation solutions. The liver cells are dissociated by sequential infusions of ethylene diamine tetraacetic acid (50 mM) and collagenase (1 to 20 mg/ml) in Krebs-Henseleit buffer, pH 7.4. Adequate perfusion of the liver is indicated by uniform blanching of the liver. Isolated cells are collected and introduced into the cell compartment (compartment 2) of the one-sided multi-coaxial hollow fiber bioreactor.

Nuclear magnetic resonance (NMR) is performed using an NMR probe design composed of two Helmholtz coils photo-etched onto flexible copper-coated composite. The two coils, suitably insulated, are wrapped around the bioreactor and oriented orthogonally to each other. The inner coil is tuned to 81 MHz for study of energy metabolism as measured by changes in the spectrum of $^{31}$P. The probe and bioreactor assembly is placed on a centering cradle in the isocenter of the magnet for optimal comparison of spectra. The aerated nutrient medium is supplied to the first compartment inlet port of the bioreactor. Integral aeration is provided by flow of a 95% air with 5% $CO_2$ mix through inlet port 4, associated with the outermost or fourth compartment of the bioreactor. Ham's F-12 nutrient medium is pumped through compartment 3 with a peristaltic pump. The temperature of the reservoir of medium is maintained at 42° C. with a temperature controlled water bath, so as to maintain the bioreactor temperature at 37° C. The NMR signal from $\gamma$-$^{31}$P nucleotide triphosphates and $\beta$-$^{31}$P nucleotide diphosphates, other cellular components of energy metabolism, and biosynthesis are analyzed. The NMR signal is monitored as a function of mass transfer dictated by gas flow rate and oxygen percentage, nutrient medium flow rates, and cell loading densities.

6.2 Oxygen Flux in the Absence of Cells.

Oxygen microelectrodes are connected to a transducer and Workbench™ software, and then calibrated against known standards. The calibrated oxygen microelectrodes are placed at intervals along the fiber length in compartment 2 of the multi coaxial hollow fiber bioreactor. A reservoir of plasma is attached to the inlet port of compartment 1, the innermost compartment of the multi-coaxial hollow fiber bioreactor. A reservoir of RPMI 1640 nutrient medium is attached to the inlet port of compartment 3. Peristaltic pumps are arranged in-line to circulate the plasma and nutrient medium. Compartment 2 is also filled with nutrient medium. The signal from each microelectrode is acquired at ten-second intervals and processed by the software for conversion to oxygen tensions. The gas phase is switched between 95% air with 5% $CO_2$ and 95% $N_2$ with 5% $CO_2$ at selected intervals. Rates of depletion and recovery of oxygen tension are measured at different flow rates to evaluate oxygen flux in the absence and presence of cells.

6.3 Use as an Extracorporeal Liver Assist Device for Evaluation of Bilirubin.

Background. The Gunn rat model, which is the animal model for Crigler-Naijar syndrome in humans is an ideal model for demonstrating the efficacy of the bioreactor as an extracorporeal liver assist device. The Gunn rat has a defect inherited as an autosomal recessive trait in Wistar rats. The defect, present in homozygous recessive animals, is in the gene encoding UDP-glucuronosyltransferase, an enzyme necessary for the conjugation and biliary excretion of bilirubin (a breakdown product of hemoglobin in senescent red blood cells). The Gunn rat therefore cannot conjugate and excrete bilirubin and becomes hyperbilirubinemic, having serum bilirubin levels of about 5–20 mg/dL, compared with 1 mg/dL in normal rats. Experimental Protocol. A scaled-up multi-coaxial hollow fiber bioreactor is used as an extracorporeal liver assist device with Gunn rats. The livers of heterozygous (phenotypically normal) Gunn rats are perfused and the cells are isolated. The cells are suspended in Dulbecco's Modified Eagle Medium (DMEM) and $10^9$ cells are introduced into the second compartment of the bioreactor. Blood from the femoral artery of a Gunn rat (total average blood volume ca. 10 to 12 mL) is perfused through compartment 3 of the bioreactor, separated from the liver cell annular space by the wall of the hollow fiber, at a flow rate of about 0.6–0.8 mL/min with the aid of a peristaltic pump. At the same time, DMEM is flowed through the compartment one of the bioreactor at a flow rate of about 0.5 mL/min. Blood flowing out of the bioreactor is returned to the Gunn rat.

The levels of unconjugated and conjugated bilirubin in blood exiting the bioreactor are determined over the course of six hours using the Sigma Total and Direct Bilirubin assay system according to the instruction supplied by Sigma Chemical Company (Sigma Procedure #522/553).

6.4 Biosynthetic Hepatocyte Function in a Scaled-Up Multi-Coaxial Hollow Fiber Bioreactor/BAL.

Liver cells isolated as in Example I are further separated by zonal centrifugation in sucrose density gradients. Density fractions corresponding to parenchymal cells are collected and introduced into the aseptic cell compartment (compartment 2) of the scaled-up multi-coaxial bioreactor.

The parenchymal cells are maintained by circulating warm Ham's F-12 nutrient medium through compartments 1 and 3, and 95% air with 5% $CO_2$ through compartment 4. The effluent from compartment 1 is collected and fractions are analyzed for parameters of biosynthetic liver function. Albumin synthesis is measured by enzyme-linked immunosorbent assay.

6.5 Biotransformatory Function in a Scaled-Up Multi-Coaxial Hollow Fiber Bioreactor/BAL.

Liver cells isolated as in Example I are further separated by zonal centrifugation in sucrose density gradients. Density fractions corresponding to Kupffer cells are collected and introduced into the compartment 2 (cell compartment) of the scaled-up multi-coaxial hollow fiber bioreactor.

The cells in the bioreactor are maintained by circulating DMEM (without Phenol Red) through the inlet and outlet ports for compartments 1 and 3 and 95% air with 5% $CO_2$ through the ports for compartment 4. The cells are permitted to adhere within the compartment, followed by the introduction of free hemoglobin (1–10 mg/ml) into compartment 1. The appearance of hemoglobin and the metabolic products of hemoglobin in compartment 3 are monitored with an in-line spectrophotometer.

6.6 The Serially-Linked Bioreactor with Human Cells for Patient Treatment.

Human hepatoma C3A cells are cultured as described (Mickelson, J. K. et al. *Hepatology* 1995, 22, 866) and introduced into all the second compartments of the serially-linked bioreactor. Nutrient medium and 95% air with 5% $CO_2$ are pumped through the third and outermost compartments, respectively, and cell growth is monitored by glucose utilization. When the cells have attained the plateau, or stationary, growth phase, the albumin output is monitored.

The blood of a patient suffering liver failure is separated into plasma and cells by plasmapheresis and the plasma is pumped into the first compartment of the first bioartificial liver subunit. A portion of the plasma flows radially from the first compartment through the cell compartment to the third compartment to form biotransformed effluent. The plasma exits the first compartment of the first bioartificial liver subunit and flows into the third compartment of the second bioartificial liver subunit. The biotransformed effluent from the third compartment of the first bioartificial liver subunit flows into the first compartment of the second bioartificial subunit. Radial flow in the first bioartificial liver subunit detoxifies a portion of the plasma and radial flow in the second bioartificial liver subunit contributes biosynthetic products to the plasma to form supplemented plasma. Vital signs, jaundice, and blood level of toxins are monitored at regular intervals. Flow rates of plasma and medium are adjusted to maximize biotransformation of circulating toxins. Survival of the patient is measured.

6.7 Extracellular Matrix Effects on Differentiation of Hepatocytes in the Scaled-Up Multi-Coaxial Hollow Fiber Bioreactor.

Parenchymal cells are isolated by zonal centrifugation as in example IV, above, suspended in reconstituted basement matrix from the Englebreth-Holm-Swarm mouse sarcoma, and introduced into the compartment 2 (cell compartment) of the scaled-up multi-coaxial bioreactor. The hepatocytes are arrested in a $G_0$ state by adhesion to the basement matrix, and are maintained in the normal hepatic phenotype (Rana et al., 1994). The highly differentiated state is characterized by synthesis of albumin and hepatic transcription factors such as C/EBP-. The parenchymal cells are maintained by circulating warm Ham's F-12 nutrient medium through compartments 1 and 3, and 95% air with 5% $CO_2$ through compartment 4. The effluent from compartment 1 is collected and fractions are analyzed for parameters of biosynthetic liver function. Albumin synthesis is measured by enzyme-linked immunosorbent assay.

6.8 Growth and Differentiation of Human Hepatocytes in the Scaled-Up Multi-Coaxial Hollow Fiber Bioreactor.

Human parenchymal hepatocytes are isolated by the method of (Block, G. D. et al. *J Cell Biol* 1996, 132, 1133) and introduced into compartment 2 of the scaled-up multi coaxial hollow fiber bioreactor. The parenchymal cells are propagated by exposure to hepatocyte growth factor (HGF/SF), epidermal factor, and transforming growth factor alpha in nutrient medium HGM introduced into compartment 3 and air:$CO_2$ (19:1) introduced into compartment 4. The ratio of transcription factor C/EBP to C/EBP is decreased by this process and the cell synthesis of albumin also is decreased. The medium flowing through compartment 3 is modified to include transforming growth factor and epidermal growth factor to induce differentiation of the cells and synthesis of albumin, in the formulation described (Sanchez, A. et al. *Exp Cell Res* 1998, 242, 27).

6.9 Biosynthesis of Hormones and Factors in the Scaled-Up Multi-Coaxial Hollow Fiber Bioreactor.

Parathyroid glands are obtained aseptically, minced, and treated with collagenase as described (Homicek, F. L. et al. *Bone Miner* 1988, 4, 157). The dispersed cells are suspended in CMRL-1415 nutrient medium supplemented with fetal bovine serum and introduced into compartment 2 of the scaled-up multi-coaxial bioreactor. A mixture of 95% air and with 5% $CO_2$ is pumped through port 4. Warm medium is pumped through ports 1 and 3 and the effluent from the chamber is concentrated by ultrafiltration for collection of parathyroid hormone, parathyroid hypertensive factor, and other cell products. The hormones and factors are purified by immunoprecipitation and chromatography.

6.10 The Five Compartment Serially-Linked Bioreactor with Human Cells for Patient Treatment.

Human hepatoma C3A cells are grown as in example VI, above, except in the third compartment of a five-compartment serially-linked bioreactor. The innermost compartment (compartment 1) and the outermost compartment (compartment 5) are suffused with the gas mix, 95% air with 5% $CO_2$. Nutrient medium is pumped through the second and fourth compartments, respectively, and cell growth is monitored by glucose utilization. When the cells have attained the plateau, or stationary, growth phase, the albumin output is monitored.

The blood of a patient suffering liver failure is separated into plasma and cells by plasmapheresis and the plasma is pumped through the serially connected second compartments of the bioreactor. Vital signs, jaundice, and blood level of toxins are monitored at regular intervals. Flow rates of plasma and medium are adjusted to maximize biotransformation of circulating toxins. Survival of the patient is measured.

6.11 Construction of the Five Compartment Serially-Linked Bioreactor with Tight-Packed Fiber Arrangement and use with Human Cells for Patient Treatment.

Bioreactor subunits are constructed with 300 outermost coaxial fibers (3 millimeter o.d.) forming a part of the outer boundary of the annular cell compartments. A hollow fiber of 1.3 millimeter o.d. is inserted into each of the 3 millimeter fibers, forming part of the inner boundary of the annular cell compartments and part of the outer boundary of the compartments number 2. One micro bore hollow fiber (300 μm o.d.) is inserted into each of the 1.3 millimeter fibers as the innermost compartment of each coaxial fiber module and another set of 300 microfibers is placed parallel and adjacent to the coaxial modules. Both sets of microfibers carry aeration gas to oxygenate the plasma and the medium. The outermost compartment is compartment number 4 and is formed by the outside of the outermost coaxial fibers (of 3 millimeter o.d.), the outside of the microfibers that are adjacent to the coaxial modules, and the inside of the housing.

The serially-linked bioreactor and associated tubing and connections are sterilized.

Human hepatocytes are isolated as in Example VIII and introduced into the annular cell compartments, compartments 3, of each of two bioreactor subunits. The hepatocyte cells are propagated by exposure to nutrient medium and growth factors described in Example VII until the cell density is sufficient for treatment of a patient in liver failure. The bioreactor subunits with a complement of viable liver cells are now termed BAL subunits.

In use for patient treatment, patient plasma enters compartment number 2 of the first BAL subunit, through the first plasma entrance port, media enters compartment number 4 of the first BAL through the first media entrance port and gas enters the first BAL through first gas entrance port. Radial flow in the first subunit is produced by a pressure gradient across the fibers, such that the hydraulic pressure in the plasma compartment is higher than the pressure in the cell or media compartments. In consequence, part of the plasma flows from compartment number 2 through the annular cell compartment into compartment number 4. In the process the liver cells in the cell compartment can biologically detoxify the plasma passing through the cell compartment. As the detoxified plasma flows into compartment 4 the medium is modified with a detoxified plasma component. The remaining plasma then exits the first BAL subunit through the first plasma exit port, media exits the first BAL subunit through the first compartment number 4 exit port and gas exits the first BAL subunit through the first gas exit port. The flow scheme is then switched in the second subunit such that the fluid (medium containing detoxified plasma) from the first compartment number 4 exit port enters the second BAL subunit through the second compartment number 2 entrance port. Similarly, plasma from first compartment 2 exit port enters the second BAL subunit through the second compartment 4 entrance port and gas enters the second BAL subunit through the second gas entrance port. A portion of the media flows radially from the compartment number 2 entrance port through the annular cell layer and into the second compartment number 4. The liver cells add proteins and other biosynthetic products to the medium that flows through the cell compartment in subunit 2. As this enriched medium flows into the remaining plasma, the resultant, modified plasma is in part detoxified and in part enriched with biosynthetic proteins. The remaining medium then exits the second BAL subunit through the second compartment 2 exit port, the modified plasma exits the second BAL subunit through the second compartment 4 exit port and gas exits the second BAL subunit through the second gas exit port. The modified plasma, effluent from second compartment 4, is returned to the patient to sustain life.

6.12 Manufacture of Scaled Up Multi-Coaxial Hollow Fiber Bioreactor.

An apparatus is used to assemble a bioreactor in which a vacuum head, that is attached as necessary to a negative pressure source, holds a bundle of hollow fibers against a mesh for rapid insertion of smaller fibers. The opposite end of the hollow fibers is inserted into a manifold and placed in a vessel. Polyurethane epoxy is applied to bond the hollow fibers to the manifold and the assembly of manifold, epoxy, and hollow fibers subjected to a centrifugal force to remove epoxy from the inside of the fibers. Upon curing, the free ends of the hollow fibers are trimmed with a saw. The process is repeated for insertion of the next smaller set of hollow fibers by applying the vacuum, gluing the ends to the next manifold, centrifuging, and trimming.

The purpose of the above description and examples is to illustrate some embodiments of the present invention without implying any limitation. It will be apparent to those of skill in the art, in light of this teaching, that various modifications and variations may be made to the composition and methods in the present invention to generate additional embodiments without departing from the spirit or scope of the invention. The specific composition of the various elements of the bioreactor system, for example, should not be construed as a limiting factor. Accordingly, it is to be understood that the drawings and descriptions in this disclosure are proffered to facilitate comprehension of the invention and should not be construed to limit the scope thereof.

All patents and publications cited herein are incorporated by reference in their entireties.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A bioreactor, comprising:
   (a) a housing having an inner side comprising: a gas introduction means integral to the housing; and a gas expiration means integral to the housing;
   (b) a plurality of modules of hollow fibers, residing within the housing, each module comprising:
      (i) at least three coaxially arranged hollow fibers, each hollow fiber having an inner side and an outer side, including an innermost hollow fiber and an outermost hollow fiber;
      (ii) at least three compartments, comprising: a first compartment defined by an inner side of an innermost hollow fiber and at least two compartments defined by a respective annular space between adjacent fibers of the at least three coaxially arranged hollow fibers; and
   (c) an outermost compartment defined by a space within the inner side of the housing which is not occupied by the plurality of modules;
   in which at least one compartment is charged with a gaseous nutrient substantially free of non-gaseous fluids.

2. The bioreactor of claim 1, where the hollow fibers are semipermeable.

3. The bioreactor of claim 2, where the hollow fibers comprise a material selected from the group consisting of polysulfone, polypropylene, nylon, polyester, polytetrafluoroethylene, cellulose acetate, and mixed esters of cellulose.

4. The bioreactor of claim 1, where the first compartment, the at least one additional compartment and the outermost compartment each further comprise at least one inlet port and at least one outlet port.

5. The bioreactor of claim 4, where the housing further comprises at least one inlet manifold and at least one outlet manifold for the first compartment and at least one inlet manifold and at least one outlet manifold for each additional compartment.

6. The bioreactor of claim 5, further comprising: microfibers substantially parallel to the modules of hollow fibers.

7. The bioreactor of claim 6, where the microfibers further comprise at least one aeration inlet port and at least one aeration outlet port.

8. The bioreactor of claim 5, where the housing has a first end and a second end, and
where each inlet port and each exit port are at the first end of the housing.

9. The bioreactor of claim 5, where at least one manifold further comprises a flow distributor.

10. The bioreactor of claim 9, where at least one compartment further comprises an extracellular matrix.

11. The bioreactor of claim 1, where the bioreactor further comprises at least $10^9$ cells.

12. The bioreactor of claim 11, where the cells are liver cells.

13. The bioreactor of claim 12, where the liver cells are selected from the group consisting of porcine liver cells and human liver cells.

14. A method of supplying cell biosynthesis products to a patient in need thereof, comprising: pumping intravenous feeding solution through a compartment of the bioreactor of claim 5; collecting the output; and intravenously feeding the output to the patient.

15. The bioreactor of claim 1, where at least one annular space is about 0.2 millimeters to about 0.8 millimeters.

16. The bioreactor of claim 1, where the bioreactor is sterilized by a means selected from the group consisting of autoclaving, ethylene oxide and gamma radiation.

17. The bioreactor of claim 1, wherein the innermost hollow fiber has a length of about 2 centimeters to about 50 centimeters.

18. The bioreactor of claim 1, where at least one coaxial hollow fiber is saturated with perfluorocarbon.

19. The bioreactor of claim 1, where at least one coaxial hollow fiber has a pore size less than $1 \times 10^{-6}$ m.

20. The bioreactor of claim 1, where at least one coaxial hollow fiber has a pore size less than $0.05 \times 10^{-6}$ m.

21. The bioreactor of claim 1, where at least one coaxial hollow fiber has a pore size less than $0.1 \times 10^6$ m.

22. The bioreactor of claim 1, where at least one compartment further comprises cells mixed with an extracellular matrix.

23. The bioreactor of claim 1 in which the gaseous nutrient includes oxygen.

24. The bioreactor of claim 23 in which the gaseous nutrient further includes carbon dioxide.

25. The bioreactor of claim 1 in which the gaseous nutrient includes air.

26. A serially-linked bioreactor, comprising a plurality of bioreactor subunits, each bioreactor subunit comprising:
(a) a housing having an inner side comprising: a gas introduction means integral to the housing; and a gas expiration means integral to the housing;
(b) a plurality of modules of hollow fibers, residing within the housing, each module comprising:
(i) at least three coaxially arranged hollow fibers, each hollow fiber having an inner side and an outer side, including an innermost hollow fiber and an outermost hollow fiber;
(ii) at least three compartments, comprising: a first compartment defined by an inner side of an innermost hollow fiber; and at least two compartments defined by a respective annular space between adjacent fibers of the at least three coaxially arranged hollow fibers; and
(c) an outermost compartment defined by a space within the inner side of the housing which is not occupied by the plurality of modules; and
(d) at least one compartment of one bioreactor subunit linked serially to at least one compartment of at least one other bioreactor subunit;
in which at least one compartment is charged with a gaseous nutrient substantially free of non-gaseous fluids.

27. The bioreactor of claim 26, where each bioreactor subunit further comprises at least $10^9$ cells.

28. The bioreactor of claim 27, where the cells are liver cells.

29. The bioreactor of claim 28 where the cells are selected from the group consisting of human liver cells and porcine liver cells.

30. The bioreactor of claim 27, where at least one compartment of each bioreactor subunit further comprises an extracellular matrix.

31. A method of treating a patient in need thereof comprising:
(a) introducing plasma of a patient into a bioreactor subunit of the serially linked bioreactor of claim 26,
(b) forcing at least a portion of the plasma to flow radially through a cell compartment of the bioreactor subunit to form a biotransformed effluent;
(c) introducing the biotransformed effluent into a second bioreactor subunit of the bioreactor of claim 26;
(d) forcing at least a portion of the biotransformed effluent to flow radially through a cell compartment of the second bioreactor subunit to form supplemented plasma; and
(e) returning the supplemented plasma to the patient's circulatory system.

32. The method of claim 31 in which the gaseous nutrient includes oxygen.

33. The method of claim 32 in which the gaseous nutrient further includes carbon dioxide.

34. The method of claim 31 in which the gaseous nutrient includes air.

35. The serially linked bioreactor of claim 26 in which the gaseous nutrient includes oxygen.

36. The serially linked bioreactor of claim 35 in which the gaseous nutrient further includes carbon dioxide.

37. The serially linked bioreactor of claim 26 in which the gaseous nutrient includes air.

* * * * *